(12) United States Patent
Richards et al.

(10) Patent No.: US 12,194,275 B2
(45) Date of Patent: *Jan. 14, 2025

(54) SMART WEARABLE INJECTION AND/OR INFUSION DEVICE

(71) Applicant: Becton, Dickinson and Company, Franklin Lakes, NJ (US)

(72) Inventors: Andrew Richards, Durham, NC (US); Michael Yarger, Chapel Hill, NC (US); David E. Booth, Frederick, MD (US); Peter Quinn, Ridgewood, NJ (US); Mircea Despa, Cary, NC (US); Adam Martin, Holly Springs, NC (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 48 days.

This patent is subject to a terminal disclaimer.

(21) Appl. No.: 18/089,152

(22) Filed: Dec. 27, 2022

(65) Prior Publication Data
US 2023/0130563 A1    Apr. 27, 2023

Related U.S. Application Data

(63) Continuation of application No. 15/942,804, filed on Apr. 2, 2018, now Pat. No. 11,541,167.
(Continued)

(51) Int. Cl.
*A61M 5/142*   (2006.01)
*A61M 5/20*    (2006.01)
(Continued)

(52) U.S. Cl.
CPC ........ *A61M 5/14244* (2013.01); *A61M 5/20* (2013.01); *A61M 5/24* (2013.01);
(Continued)

(58) Field of Classification Search
CPC ............... A61M 5/14244; A61M 5/24; A61M 5/31545; A61M 5/31556; A61M 5/281;
(Continued)

(56) References Cited

U.S. PATENT DOCUMENTS

| | | |
|---|---|---|
| 8,715,224 B2 | 5/2014 | Kamen et al. |
| 8,740,838 B2 | 6/2014 | Hemond et al. |
| 10,155,090 B2 | 12/2018 | Larsen et al. |
| 2005/0214129 A1 | 9/2005 | Greene et al. |
| 2007/0093752 A1 | 4/2007 | Zhao et al. |

(Continued)

FOREIGN PATENT DOCUMENTS

| | | |
|---|---|---|
| CN | 101247844 A | 8/2008 |
| CN | 205658923 U | 3/2014 |

(Continued)

*Primary Examiner* — Kami A Bosworth
*Assistant Examiner* — Avery Smale
(74) *Attorney, Agent, or Firm* — The Webb Law Firm

(57) ABSTRACT

A delivery device for delivering a medical fluid to a patient has a housing configured for receiving a container at least partially filled with the medical fluid. The delivery device further has a drive mechanism associated with the housing configured for delivering the medical fluid from the container to the patient in a dosing procedure. The delivery device further has a module configured for detecting at least one of a property of the dosing procedure and a property of the medical fluid. The module has at least one dose detection sensor configured for detecting an initiation, progression, and completion of the dosing procedure based on a position of a stopper within the container. The module further has at least one temperature sensor configured for measuring a temperature of the medical fluid within the container based on a temperature of the container.

19 Claims, 19 Drawing Sheets

Related U.S. Application Data

(60) Provisional application No. 62/479,742, filed on Mar. 31, 2017.

(51) Int. Cl.
  *A61M 5/24* (2006.01)
  *A61M 5/28* (2006.01)
  *A61M 5/315* (2006.01)

(52) U.S. Cl.
  CPC ........ *A61M 5/281* (2013.01); *A61M 5/31545* (2013.01); *A61M 5/31556* (2013.01); *A61M 2005/14272* (2013.01); *A61M 2005/2006* (2013.01); *A61M 2205/33* (2013.01); *A61M 2205/3306* (2013.01); *A61M 2205/3334* (2013.01); *A61M 2205/3368* (2013.01); *A61M 2205/581* (2013.01)

(58) Field of Classification Search
  CPC ............ A61M 5/20; A61M 2205/3368; A61M 2205/33; A61M 2205/3334; A61M 2005/2006; A61M 2205/3306; A61M 2005/14272; A61M 2205/581; A61M 2205/3553; A61M 2205/60; A61M 2205/6009; A61M 2005/14268; A61M 5/3157; A61M 5/31568; A61M 5/31566
  See application file for complete search history.

(56) References Cited

U.S. PATENT DOCUMENTS

| | | |
|---|---|---|
| 2008/0191013 A1 | 8/2008 | Liberatore |
| 2011/0224613 A1 | 9/2011 | D'Antonio et al. |
| 2011/0313351 A1* | 12/2011 | Kamen ............... A61M 5/1452 604/67 |
| 2015/0209505 A1 | 7/2015 | Hanson et al. |
| 2015/0246176 A1 | 9/2015 | Navarro et al. |
| 2016/0030673 A1 | 2/2016 | White et al. |
| 2016/0030683 A1 | 2/2016 | Taylor et al. |
| 2016/0310680 A1 | 10/2016 | Kataoka et al. |

FOREIGN PATENT DOCUMENTS

| | | |
|---|---|---|
| CN | 103957961 A | 7/2014 |
| CN | 105194766 A | 12/2015 |
| JP | 2013517841 A | 5/2013 |
| JP | 2013539689 A | 10/2013 |
| JP | 2016500013 A | 1/2016 |
| WO | 2011091246 A2 | 7/2011 |
| WO | 2013073650 A1 | 5/2013 |
| WO | 2015123688 A1 | 8/2015 |
| WO | 2015136513 A1 | 9/2015 |
| WO | 2015187793 A1 | 12/2015 |
| WO | 2015187797 A1 | 12/2015 |
| WO | 2016019375 A1 | 2/2016 |
| WO | 2016115372 A1 | 7/2016 |
| WO | 2016118736 A1 | 7/2016 |
| WO | 2017009724 A1 | 1/2017 |
| WO | 2017114911 A1 | 7/2017 |

* cited by examiner

SMART WEARABLE INJECTION AND/OR INFUSION DEVICE

CROSS-REFERENCE TO RELATED APPLICATIONS

This application is a continuation of U.S. patent application Ser. No. 15/942,804, titled "Smart Wearable Injection and/or Infusion Device" and filed on Apr. 2, 2018, which issued as U.S. Pat. No. 11,541,167 on Jan. 3, 2023, which claims priority to U.S. Provisional Application No. 62/479,742, titled "Smart Wearable Injection and/or Infusion Device" and filed on Mar. 31, 2017, the disclosures of each of which are incorporated herein by reference in their entirety.

BACKGROUND OF THE INVENTION

Field of the Invention

The present invention relates generally to wearable injection and/or infusion devices, and in particular, to wearable injection and/or infusion devices for administrating a therapeutic agent to a patient.

Description of the Related Art

Various types of automatic injection devices have been developed to allow drug solutions and other liquid therapeutic preparations to be administered by untrained personnel or to be self-injected. Generally, these devices include a reservoir that is pre-filled with the liquid therapeutic preparation, and some type of automatic needle-injection mechanism that can be triggered by the user. When the volume of fluid or drug to be administered is generally below a certain volume, such as 1 mL, an auto-injector is typically used, which typically has an injection time of about 10 to 15 seconds. When the volume of fluid or drug to be administered is above 1 mL, the injection time generally becomes longer resulting in difficulties for the patient to maintain contact between the device and the target area of the patient's skin. Further, as the volume of drug to be administered becomes larger, increasing the time period for injection becomes desirable. The traditional method for a drug to be injected slowly into a patient is to initiate an IV and inject the drug into the patient's body slowly. Such a procedure is typically performed in a hospital or outpatient setting.

Certain devices allow for self-injection or self-infusion in a home setting and are capable of gradually injecting a liquid therapeutic preparation into the skin of a patient. In some cases, these devices are small enough (both in height and in overall size) to allow them to be "worn" by a patient while the liquid therapeutic preparation is being infused into the patient. These wearable injection and/or infusion devices typically include a pump or other type of discharge mechanism to force the liquid therapeutic preparation to flow out of a reservoir and into the injection needle. Such devices also typically include a valve or flow control mechanism to cause the liquid therapeutic preparation to begin to flow at the proper time and a triggering mechanism to initiate the injection.

While various wearable injection and/or infusion devices exist in the art, there is a need in the art for an improved wearable injection and/or infusion device.

SUMMARY OF THE INVENTION

Generally, provided is an improved wearable injection and/or infusion device configured for administrating a therapeutic agent to a patient. In some examples, the wearable injection and/or infusion device may be configured for continuous monitoring of dose progression. In other examples, the wearable injection and/or infusion device may be configured for detecting a stall in dose progression based on a detected delivery rate. In further examples, the wearable injection and/or infusion device may be configured for detecting a temperature of the therapeutic agent and adjusting at least one dose progression protocol based on a detected temperature. In other examples, the wearable injection and/or infusion device may be configured to enable external communication of data to a remote device. In further examples, the wearable injection and/or infusion device may incorporate enhanced visual indicators about a status of the device.

In some examples of the present disclosure, a delivery device for delivering a medical fluid to a patient may have a housing configured for receiving a container at least partially filled with the medical fluid. The delivery device further may have a drive mechanism associated with the housing configured for delivering the medical fluid from the container to the patient in a dosing procedure. The delivery device further may have a module configured for detecting at least one of a property of the dosing procedure and a property of the medical fluid. The module may have at least one dose detection sensor configured for detecting an initiation, progression, and completion of the dosing procedure based on a position of a stopper within the container. The module further may have at least one temperature sensor configured for measuring a temperature of the medical fluid within the container based on a temperature of the container.

In other examples of the present disclosure, the at least one dose detection sensor may be configured for measuring a rate of delivery of the medical fluid to the patient based on detecting a change in the position of the stopper as a function of time. The module may be configured to stop the drive mechanism if the rate of delivery of the medical fluid measured by the at least one dose detection sensor is below a minimum threshold or above a maximum threshold. An output of the at least one dose detection sensor may be a function of an output of at least one temperature sensor. The at least one dose detection sensor may be an optical sensor array configured to detect an actual volume of the medical fluid in the container or estimate a volume of the medical fluid in the container based on the position of the stopper within the container. The optical sensor array may have one or more infrared emitters configured to emit electromagnetic energy in an infrared spectrum and one or more infrared detectors configured to detect electromagnetic energy in the infrared spectrum.

In other examples of the present disclosure, the temperature of the medical fluid may be a function of an ambient environment temperature outside the housing of the delivery device and a local temperature within the housing of the delivery device. The module may be configured to prevent actuation of the drive mechanism if a temperature of the medical fluid within the container is below a minimum threshold or above a maximum threshold.

In other examples of the present disclosure, the module further may have at least one activation detection switch configured for detecting the initiation of the dosing procedure and at least one completion detection switch configured for detecting the completion of the dosing procedure. The at least one activation detection switch may be configured to detect at least one of a position and a velocity of at least one component of the drive mechanism and the at least one completion detection switch may be configured to detect at least one of a position and a velocity of at least one component of the drive mechanism. The at least one activation detection switch may be a mechanical sensor in direct physical contact with at least one component of the drive mechanism or an optical sensor without direct physical contact with at least one component of the drive mechanism. The at least one completion detection switch may be a mechanical sensor in direct physical contact with at least one component of the drive mechanism or an optical sensor without direct physical contact with at least one component of the drive mechanism.

In other examples of the present disclosure, the module further may have a communication element configured for external communication with a remote device via a wired connection, a wireless connection, or a combination of the wired connection and the wireless connection. The communication element may be a one-way communication element configured to send information to the remote device or receive information from the remote device, or a two-way communication element configured to send information to the remote device and receive information from the remote device. The remote device may be configured to provide at least one of contextual instructions for using the delivery device, safety protocol information about the dosing procedure, and a status indication of at least one stage of the dosing procedure.

In other examples of the present disclosure, the module further may have one or more indicators configured for providing at least one of information about a state of the dosing procedure and operation instructions to a user. The one or more indicators may have at least one visual indicator having at least one light. the at least one light is a single or multi-color light-emitting diode configured for at least one of steady state and flashing operation. The one or more indicators may have at least one audible indicator configured for delivering an audible message to a user. The delivery device may have a cover removably connectable to the housing, wherein the module is connected to the cover.

Further examples or aspects of the present disclosure are characterized in the following numbered clauses.

Clause 1. A delivery device for delivering a medical fluid to a patient, the delivery device comprising: a housing configured for receiving a container at least partially filled with the medical fluid; a drive mechanism associated with the housing configured for delivering the medical fluid from the container to the patient in a dosing procedure; and a module configured for detecting at least one of a property of the dosing procedure and a property of the medical fluid, the module comprising: at least one dose detection sensor configured for detecting an initiation, progression, and completion of the dosing procedure based on a position of a stopper within the container; and at least one temperature sensor configured for measuring a temperature of the medical fluid within the container based on a temperature of the container.

Clause 2. The delivery device of clause 1, wherein, based on detecting a change in the position of the stopper as a function of time, the at least one dose detection sensor is configured for measuring a rate of delivery of the medical fluid to the patient.

Clause 3. The delivery device of clause 1 or 2, wherein the module is configured to stop the drive mechanism if the rate of delivery of the medical fluid measured by the at least one dose detection sensor is below a minimum threshold or above a maximum threshold.

Clause 4. The delivery device of any of clauses 1-3, wherein an output of the at least one dose detection sensor is a function of an output of at least one temperature sensor.

Clause 5. The delivery device of any of clauses 1-4, wherein the at least one dose detection sensor is an optical sensor array configured to detect an actual volume of the medical fluid in the container or estimate a volume of the medical fluid in the container based on the position of the stopper within the container.

Clause 6. The delivery device of any of clauses 1-5, wherein the optical sensor array comprises one or more infrared emitters configured to emit electromagnetic energy in an infrared spectrum and one or more infrared detectors configured to detect electromagnetic energy in the infrared spectrum.

Clause 7. The delivery device of any of clauses 1-6, wherein the temperature of the medical fluid is a function of an ambient environment temperature outside the housing of the delivery device and a local temperature within the housing of the delivery device.

Clause 8. The delivery device of any of clauses 1-7, wherein the module is configured to prevent actuation of the drive mechanism if a temperature of the medical fluid within the container is below a minimum threshold or above a maximum threshold.

Clause 9. The delivery device of any of clauses 1-8, wherein the module further comprises at least one activation detection switch configured for detecting the initiation of the dosing procedure and at least one completion detection switch configured for detecting the completion of the dosing procedure.

Clause 10. The delivery device of any of clauses 1-9, wherein the at least one activation detection switch is configured to detect at least one of a position and a velocity of at least one component of the drive mechanism and wherein the at least one completion detection switch is configured to detect at least one of a position and a velocity of at least one component of the drive mechanism.

Clause 11. The delivery device of any of clauses 1-10, wherein the at least one activation detection switch is a mechanical sensor in direct physical contact with at least one component of the drive mechanism or an optical sensor without direct physical contact with at least one component of the drive mechanism.

Clause 12. The delivery device of any of clauses 1-11, wherein the at least one completion detection switch is a mechanical sensor in direct physical contact with at least one component of the drive mechanism or an optical sensor without direct physical contact with at least one component of the drive mechanism.

Clause 13. The delivery device of any of clauses 1-12, wherein the module further comprises a communication element configured for external communication with a remote device via a wired connection, a wireless connection, or a combination of the wired connection and the wireless connection.

Clause 14. The delivery device of any of clauses 1-13, wherein the communication element is a one-way communication element configured to send information to the remote device or receive information from the remote device, or a two-way communication element configured to send information to the remote device and receive information from the remote device.

Clause 15. The delivery device of any of clauses 1-14, wherein the remote device is configured to provide at least one of contextual instructions for using the delivery device, safety protocol information about the dosing procedure, and a status indication of at least one stage of the dosing procedure.

Clause 16. The delivery device of any of clauses 1-15, wherein the module further comprises one or more indicators configured for providing at least one of information about a state of the dosing procedure and operation instructions to a user.

Clause 17. The delivery device of any of clauses 1-16, wherein the one or more indicators comprises at least one visual indicator having at least one light.

Clause 18. The delivery device of any of clauses 1-17, wherein the at least one light is a single or multi-color light-emitting diode configured for at least one of steady state and flashing operation.

Clause 19. The delivery device of any of clauses 1-18, wherein the one or more indicators comprises at least one audible indicator configured for delivering an audible message to a user.

Clause 20. The delivery device of any of clauses 1-19, further comprising a cover removably connectable to the housing, wherein the module is connected to the cover.

These and other features and characteristics of the present disclosure, as well as the methods of operation and functions of the related elements or structures and the combination of parts and economies of manufacture, will become more apparent upon consideration of the following description with reference to the accompanying drawings, all of which form a part of this specification. It is to be expressly understood, however, that the drawings are for the purpose of illustration and description only and are not intended as a definition of the limits of the invention.

BRIEF DESCRIPTION OF THE DRAWINGS

In FIGS. 1-24, like characters refer to the same components and elements, as the case may be, unless otherwise stated.

DETAILED DESCRIPTION OF THE PREFERRED EXAMPLES

Figure 1:
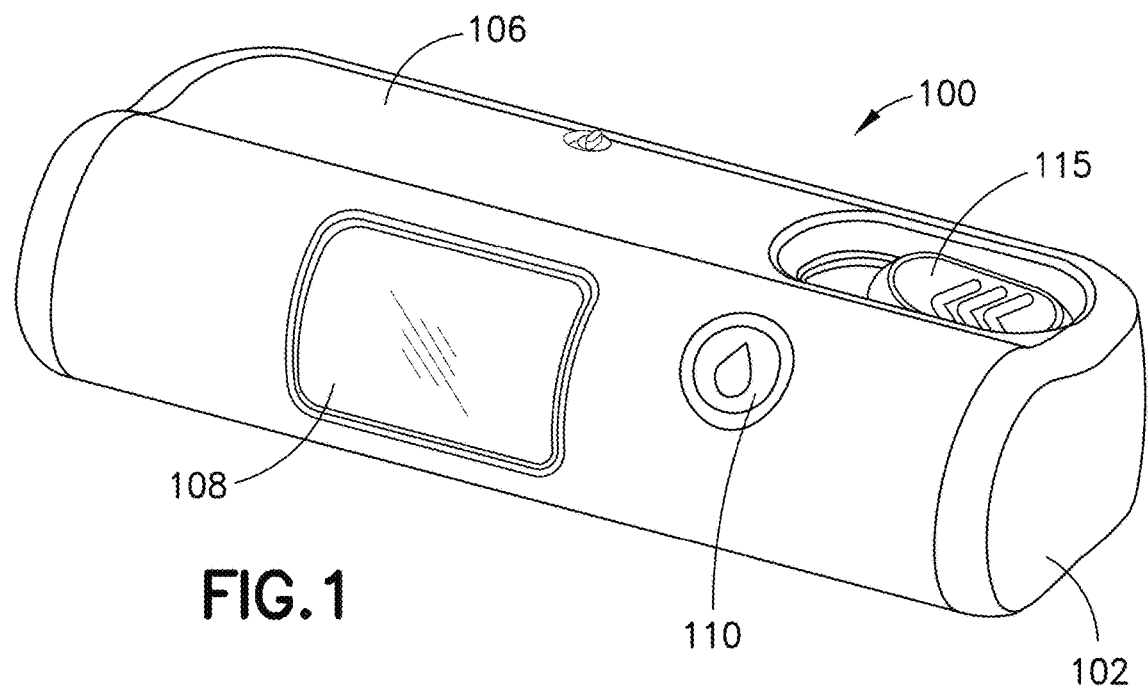
FIG. 1 is a front perspective view of a smart wearable injection and/or infusion device in accordance with one example.

As used herein, the singular form of "a", "an", and "the" include plural referents unless the context clearly dictates otherwise.

Spatial or directional terms, such as "left", "right", "inner", "outer", "above", "below", and the like, relate to the invention as shown in the drawing figures and are not to be considered as limiting as the invention can assume various alternative orientations.

All numbers and ranges used in the specification and claims are to be understood as being modified in all instances by the term "about". By "about" is meant plus or minus twenty-five percent of the stated value, such as plus or minus ten percent of the stated value. However, this should not be considered as limiting to any analysis of the values under the doctrine of equivalents.

Unless otherwise indicated, all ranges or ratios disclosed herein are to be understood to encompass the beginning and ending values and any and all subranges or subratios subsumed therein. For example, a stated range or ratio of "1 to 10" should be considered to include any and all subranges or subratios between (and inclusive of) the minimum value of 1 and the maximum value of 10; that is, all subranges or subratios beginning with a minimum value of 1 or more and ending with a maximum value of 10 or less. The ranges and/or ratios disclosed herein represent the average values over the specified range and/or ratio.

The terms "first", "second", and the like are not intended to refer to any particular order or chronology, but refer to different conditions, properties, or elements.

The term "at least" is synonymous with "greater than or equal to".

The term "not greater than" is synonymous with "less than or equal to".

As used herein, "at least one of" is synonymous with "one or more of". For example, the phrase "at least one of A, B, and C" means any one of A, B, or C, or any combination of any two or more of A, B, or C. For example, "at least one of A, B, and C" includes A alone; or B alone; or C alone; or A and B; or A and C; or B and C; or all of A, B, and C.

The term "includes" is synonymous with "comprises".

The discussion of the invention may describe certain features as being "particularly" or "preferably" within certain limitations (e.g., "preferably", "more preferably", or "even more preferably", within certain limitations). It is to be understood that the invention is not limited to these particular or preferred limitations but encompasses the entire scope of the disclosure.

In various non-limiting examples or aspects, and with reference to FIG. 1, the present disclosure is directed to a wearable injection and/or infusion device that may be configured for continuous monitoring of dose progression. In other examples, the wearable injection and/or infusion device may be configured for detecting a stall in dose progression based on a detected delivery rate. In further examples, the wearable injection and/or infusion device may be configured for detecting a temperature of the therapeutic agent and adjusting at least one dose progression protocol based on the detected temperature. In other examples, the wearable injection and/or infusion device may be configured to enable external communication of data to a remote device. In further examples, the wearable injection and/or infusion device may incorporate enhanced visual indicators about a status of the device.

Wearable Injection and/or Infusion Device

Figure 2:
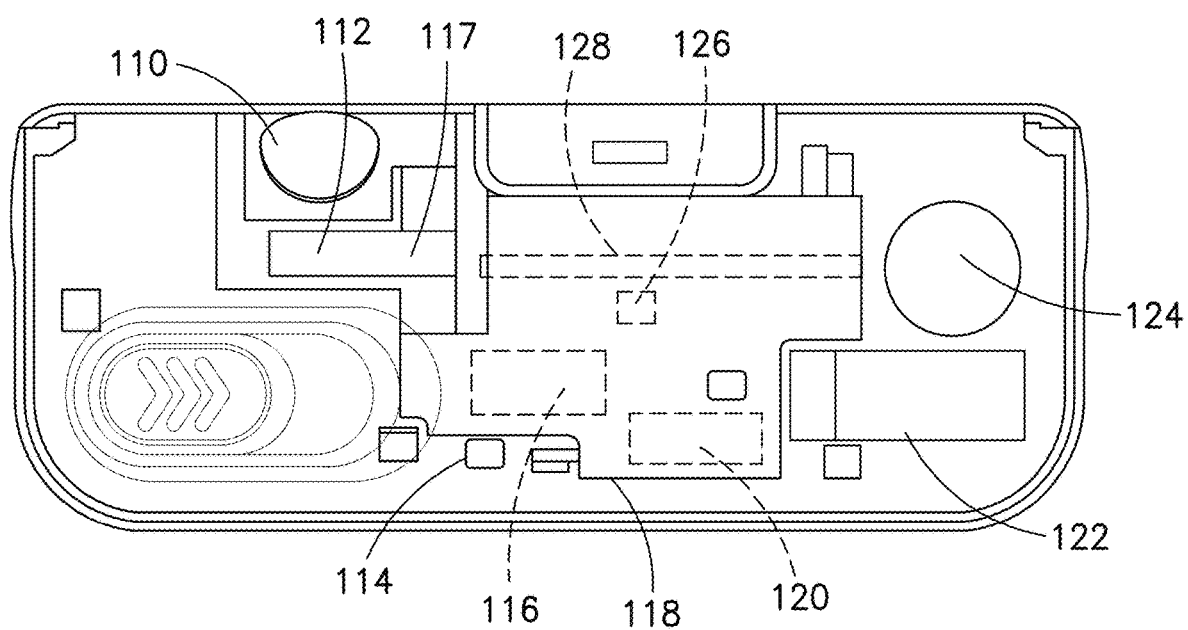
FIG. 2 is a schematic top view of the smart wearable injection and/or infusion device of FIG. 1 showing various components of the device.
Figure 3:
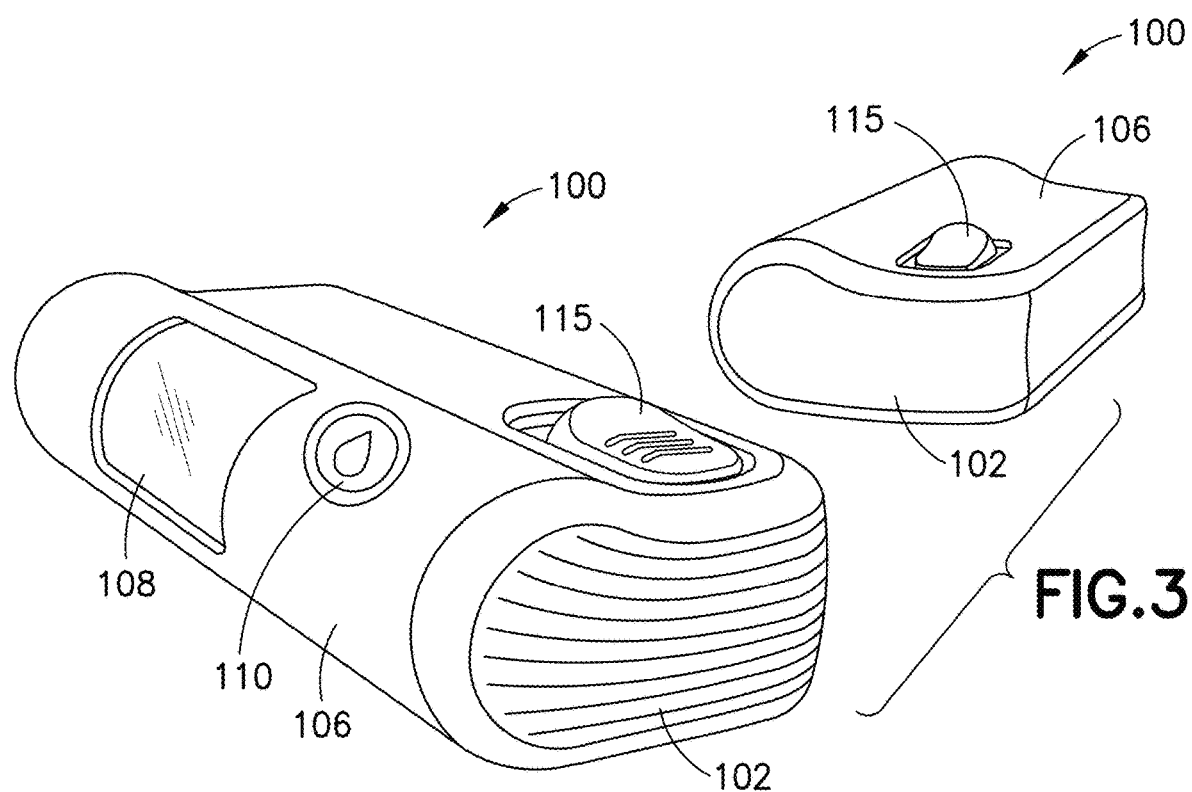
FIG. 3 is a side perspective view of the smart wearable injection and/or infusion device shown in FIG. 1.
Figure 4:
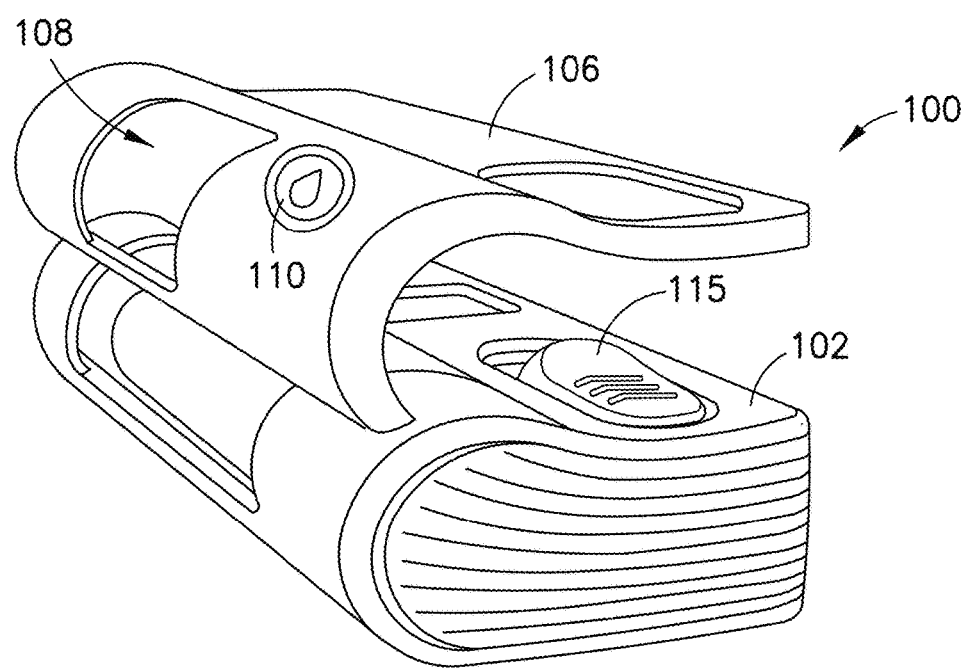
FIG. 4 is an exploded view of the smart wearable injection and/or infusion device shown in FIG. 3 showing a cover separated from the smart wearable injection and/or infusion device.
Figure 5:
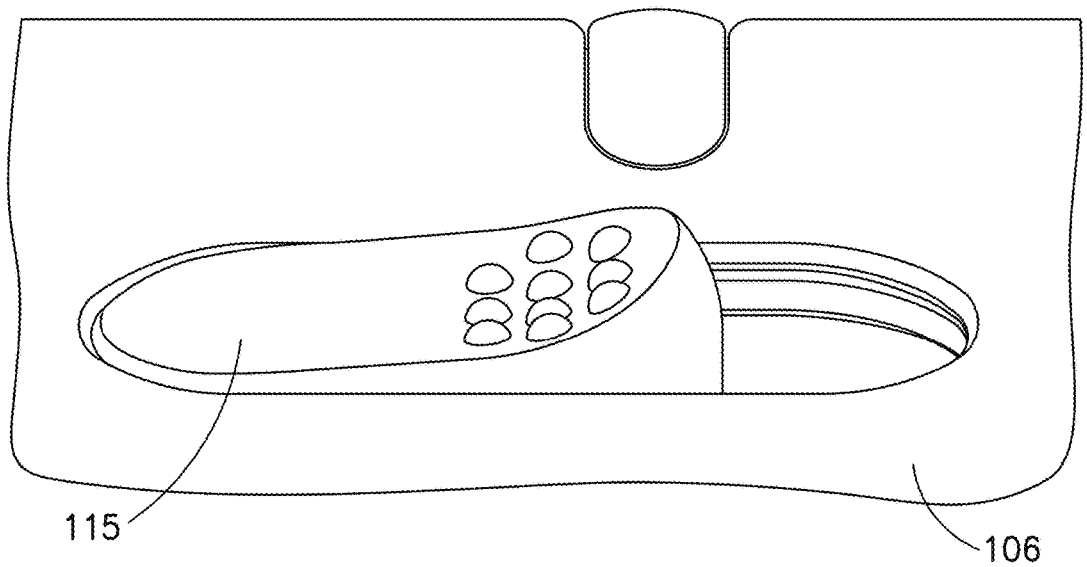
FIG. 5 is a detailed perspective view of a control element for use with a smart wearable injection and/or infusion device.

With reference to FIGS. 1-2, a wearable injection and/or infusion device 100 is shown in accordance with one example. The wearable injection and/or infusion device 100 is configured for being connected to the skin of a patient to deliver a dose of a therapeutically effective amount of a therapeutic agent at a predetermined delivery rate. For example, the therapeutic agent may be any type of drug, chemical, biological, or biochemical substance that, when delivered in a therapeutically effective amount, achieves a desired therapeutic effect. The wearable injection and/or infusion device 100 has a housing 102 for enclosing a syringe assembly 103 (shown in FIG. 7) that is in fluid communication with a container 104 (shown in FIG. 7) filled with the therapeutic agent. The wearable injection and/or infusion device 100 is operable to deliver the therapeutic agent from the container 104 to the patient using the syringe assembly 103.

Figure 6:
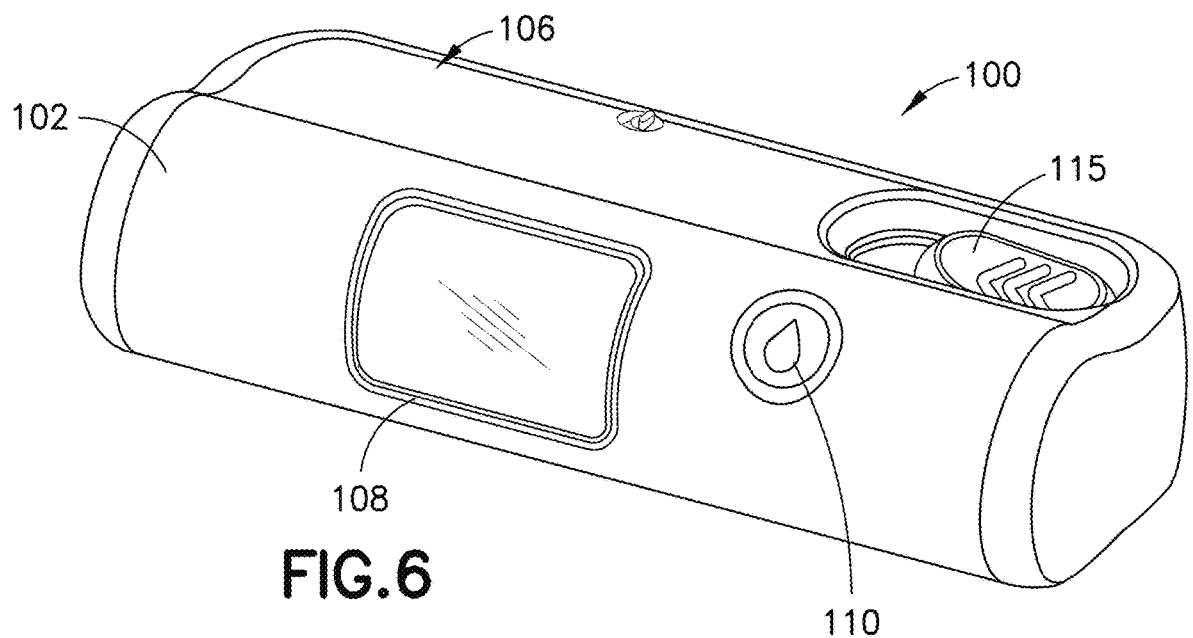
FIG. 6 is a front perspective view of a smart wearable injection and/or infusion device in accordance with another example.
Figure 7:
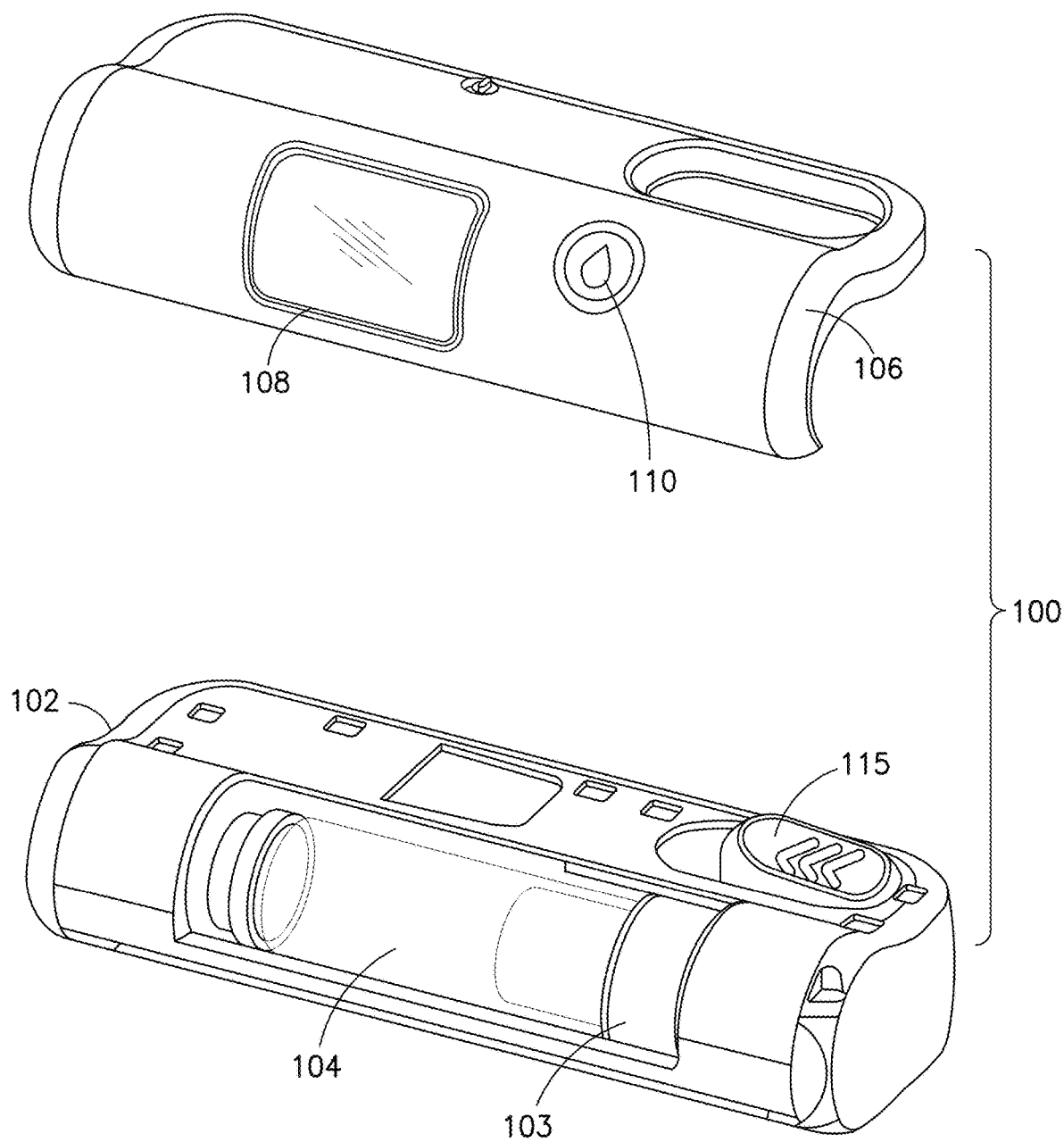
FIG. 7 is an exploded perspective view of the smart wearable injection and/or infusion device shown in FIG. 6.
Figure 8:
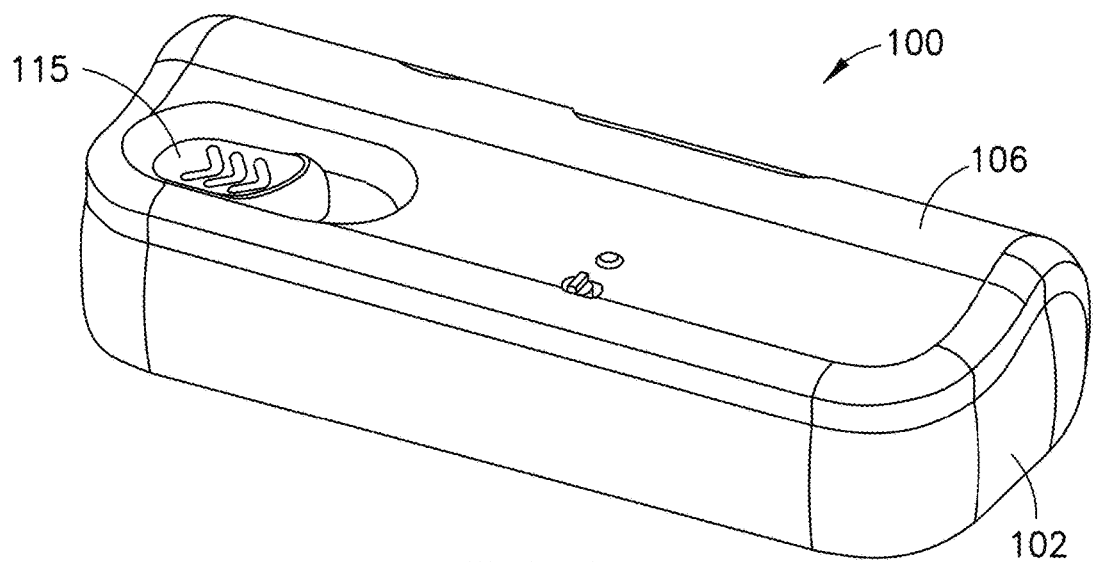
FIG. 8 is a rear perspective view of the smart wearable injection and/or infusion device shown in FIG. 6.
Figure 9:
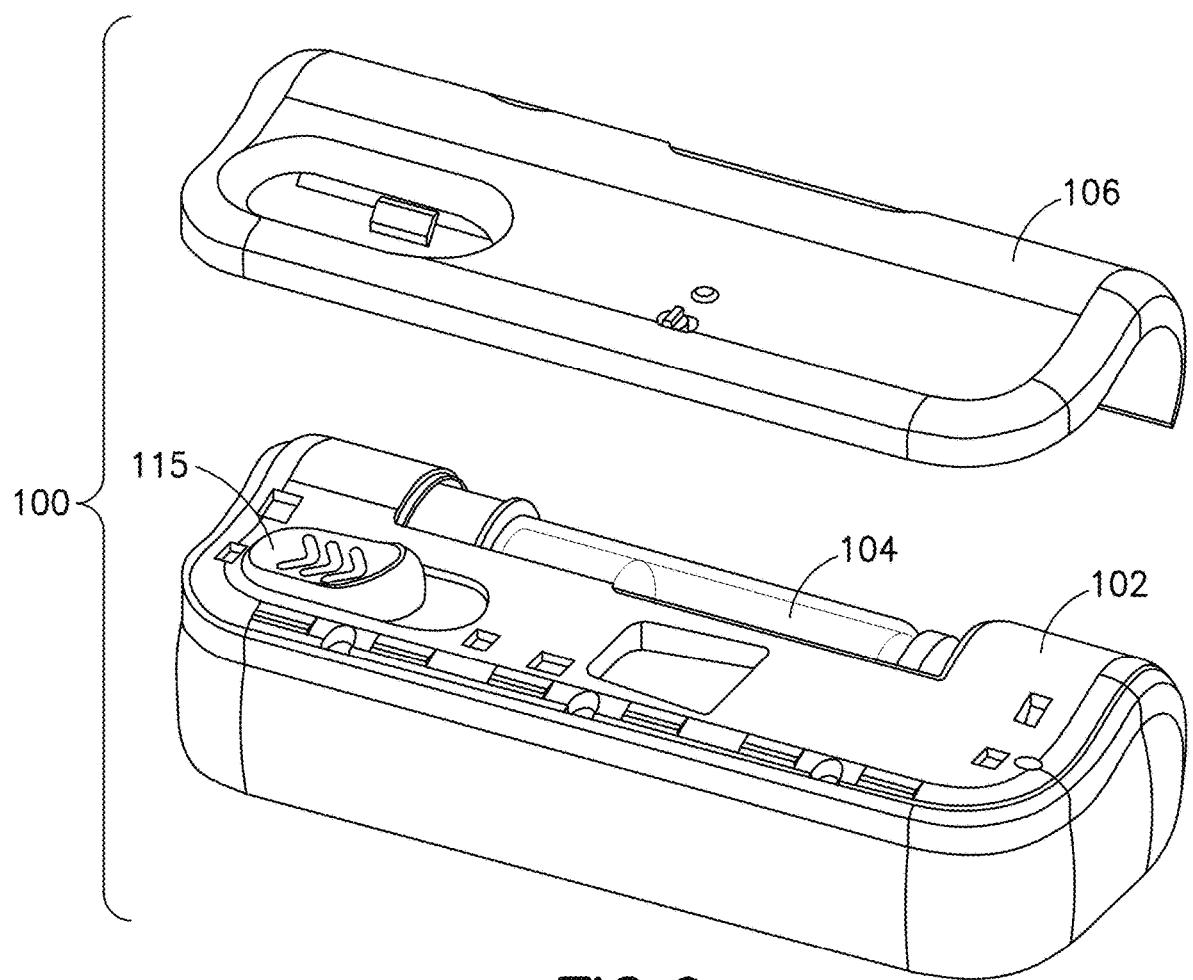
FIG. 9 is an exploded perspective view of the smart wearable injection and/or infusion device shown in FIG. 8.

With reference to FIGS. 6-7, the housing 102 of the wearable injection and/or infusion device 100 has a cover 106 that may be removably connected to the housing. The cover 106 may have a module 150 (shown in FIG. 10) comprising a plurality of components configured for dose progression, stall detection, temperature measurement, and external communication. As discussed herein, the module 150 may include one or more sensors, such as environmental sensors (e.g. temperature), to both improve the dose detection algorithms (e.g. fluid viscosity temperature effects) and to provide feedback to the user (e.g. drug is too cold for injection). The module 150 may additionally include one or more indicators (e.g. audible, visible, tactile) to provide feedback or instruction to the user. The module 150 may also include communication capabilities to transmit device data to an external device (e.g. a smartphone). The module 150 is integrated with the cover 106 such that, when the cover 106 is connected to the housing 102, the module 150 does not interfere with the underlying function of the wearable injection and/or infusion device 100. The module 150 may include additional sensors to detect mechanical motions associated with injector operation (e.g. switches to detect activation, completion, needle insertion/withdrawal, or other device events and states). The module 150 may have one or more additional sensors to continuously monitor dose delivery, such as an optical sensor array, capacitive sensor array, inductive sensor array, etc.

In some examples, the cover 106, including the module 150 may be provided as a replacement to an existing cover of an existing wearable injection and/or infusion device (not shown). In such examples, the cover 106 and the module 150 may be integrated with the wearable injection and/or infusion device to provide additional functionality to the wearable injection and/or infusion device afforded by the module 150. For example, the cover 106 may be used with the wearable injection and/or infusion device disclosed in International Patent Application No. PCT/US2016/013444 (published as WO/2016/115372), the disclosure of which is incorporated by reference herein in its entirety.

The cover 106 has a viewing window 108 for viewing the contents of the container 104, such as viewing a fill volume of the container 104. A filter (not shown) may be provided on the viewing window 108 for filtering the ambient light passing through the window 108. The housing 102 further has an indicator 110 for indicating a status of the wearable injection and/or infusion device 100.

With reference to FIG. 2, the wearable injection and/or infusion device 100 further has an activation detection switch 112 and a completion detection switch 114 for detecting an activation/completion of a dosing procedure. The wearable injection and/or infusion device 100 further has an activation detection button switch 117 to detect the state of an injector activation button 115 (shown in FIG. 1). The wearable injection and/or infusion device 100 further has a wireless communication element 116 for communication with a remote device, an on/off switch 118 for powering the device 100 on/off, and a charging port 120 for recharging a battery 122. The wearable injection and/or infusion device 100 further has an audible indicator 124, one or more temperature sensors 126, and a dose detection array 128.

Figure 23:
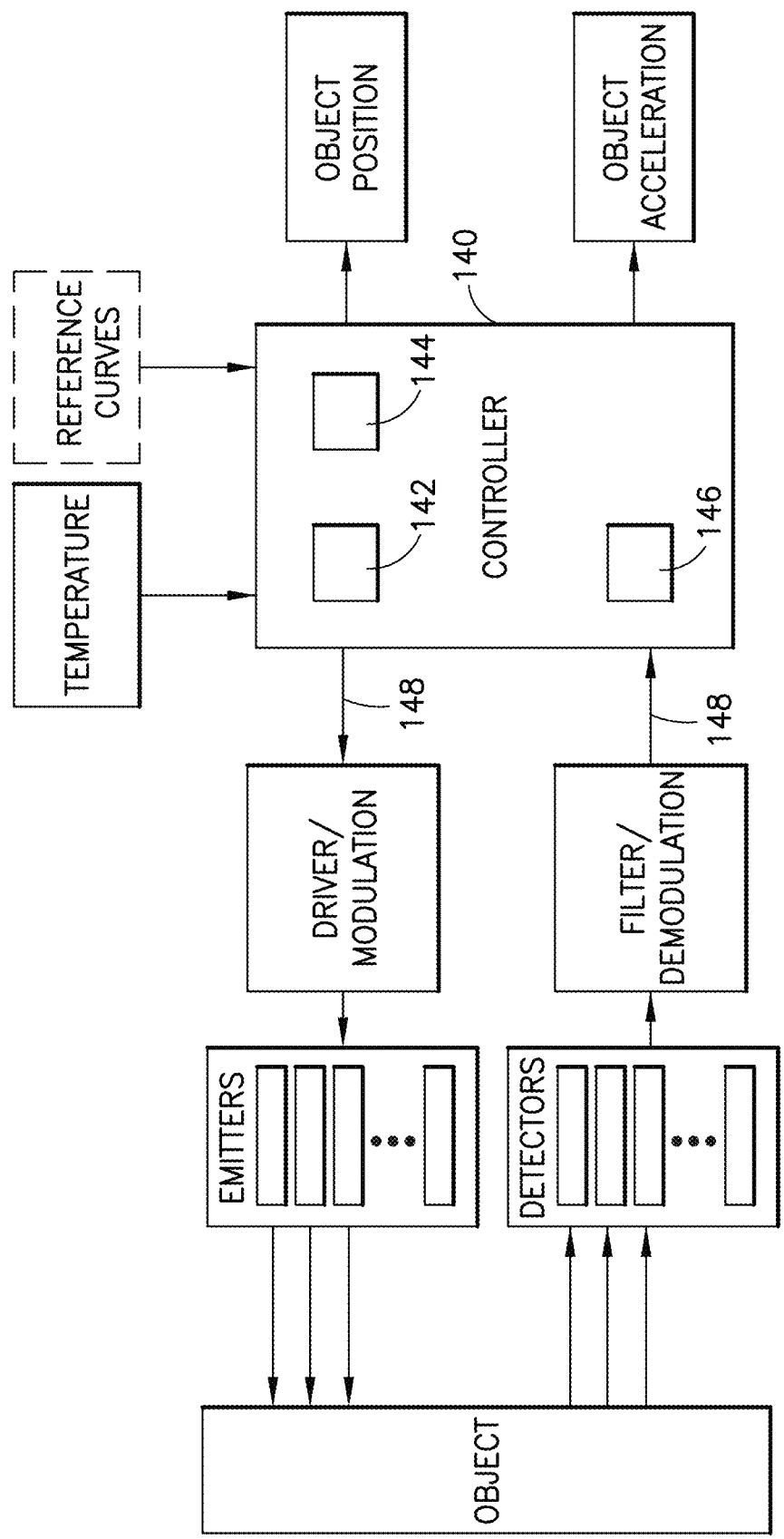
FIG. 23 is a schematic representation of various components of a smart wearable injection and/or infusion device.

With reference to FIG. 23, a controller 140 may be provided for controlling one or more of the components of the wearable injection and/or infusion device 100. In some examples, the controller 140 includes a processor 142, memory 144, storage component 146, and a bus 148 for communicating with various components of the wearable injection and/or infusion device 100. The bus 148 includes a component that permits communication among the components of the wearable injection and/or infusion device 100. In some non-limiting embodiments, processor 142 is implemented in hardware, firmware, or a combination of hardware and software. For example, the processor 142 includes a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.) that can be programmed to perform a function. Memory 144 includes a random access memory (RAM), a read only memory (ROM), and/or another type of dynamic or static storage device (e.g., flash memory, magnetic memory, optical memory, etc.) that stores information and/or instructions for use by the processor 142.

Storage component 146 stores information and/or software related to the operation and use of the wearable injection and/or infusion device 100. For example, the storage component 146 includes a hard disk (e.g., a magnetic disk, an optical disk, a magneto-optic disk, a solid state disk, etc.), a cartridge, a magnetic tape, and/or another type of computer-readable medium, along with a corresponding drive. A computer-readable medium (e.g., a non-transitory computer-readable medium) is defined herein as a non-transitory memory device. A memory device includes memory space located inside of a single physical storage device or memory space spread across multiple physical storage devices.

The wearable injection and/or infusion device 100 can perform one or more processes described herein. The wearable injection and/or infusion device 100 can perform these processes based on the processor 142 executing software instructions stored by a computer-readable medium, such as the memory 144 and/or storage component 146. Software instructions can be read into the memory 144 and/or the storage component 146 from another computer-readable medium or from another device via the bus 148. When executed, software instructions stored in the memory 144 and/or the storage component 146 cause the processor 142 to perform one or more processes described herein. Additionally, or alternatively, hardwired circuitry can be used in place of or in combination with software instructions to perform one or more processes described herein. Thus, examples described herein are not limited to any specific combination of hardware circuitry and software.

The number and arrangement of components shown in FIG. 23 are provided as an example. In some non-limiting examples, the controller 140 includes additional components, fewer components, different components, or differently arranged components than those shown in FIG. 23. Additionally, or alternatively, a set of components (e.g., one or more components) of the controller 140 can perform one or more functions described as being performed by another set of components of the wearable injection and/or infusion device 100.

Device State Detection

In some examples, the cover 106 and the module 150 may be configured to track the mechanical state of the underlying components of the wearable injection and/or infusion device 100. For example, detection switches 112, 114 within the module 150 may be configured to detect at least one characteristic of at least one component of the wearable injection and/or infusion device 100, such as a position, velocity, and/or changes in state of a component from a first state to a second state. For example, detection switches 112, 114 within the module 150 may be configured to detect the mechanical motions associated with changes in injector state, such as needle shield removal, injector unlock, activation button depression, injection activation, and injection completion. In some examples, the detection switches 112, 114 may be mechanical components, with direct mechanical interactions with the underlying components. In other examples, the detection switches 112, 114 may be infrared-based optical sensors (e.g. reflectance or photointerrupter sensors) to allow non-contact detection. Transitions in device state may be used as triggers to start or stop other system measurements such as temperature or dose progression.

Dose Progression and Stall Detection

In some examples, the wearable injection and/or infusion device 100 may be configured to monitor dose progression and detect stalling of dose progression using the module 150. For example, the dose detection array 128 of the module 150 may be an optical sensor array for tracking a dispense chain. The dose detection array 128 may be configured to detect, or estimate using an algorithm, a volume of therapeutic agent that is delivered to the patient. The dose detection array 128 may be configured so as to not contact the components of the wearable injection and/or infusion device, and therefore not impact the delivery of the therapeutic agent. For example, the dose detection array 128 may be positioned on a lateral side of the container 104. The dose detection array 128 may be configured for detecting a progression of a stopper in a longitudinal direction of the container 104 and correlate the position of the stopper with a volume of the therapeutic agent that has been delivered and/or a volume of the volume of the therapeutic agent remaining in the container 104. In some examples, the dose detection array 128 may be an optical system having one or more emitters that emit electromagnetic energy, such as visible or infrared light, that is reflected from the stopper and the container 104 to be received by one or more detectors. The reflective nature of the dose detection array 128 allows for the components to be placed on one side of the container 104. This makes a more compact and easier to manufacture system than an arrangement where emitters and detectors are positioned opposite one another.

Figure 10:
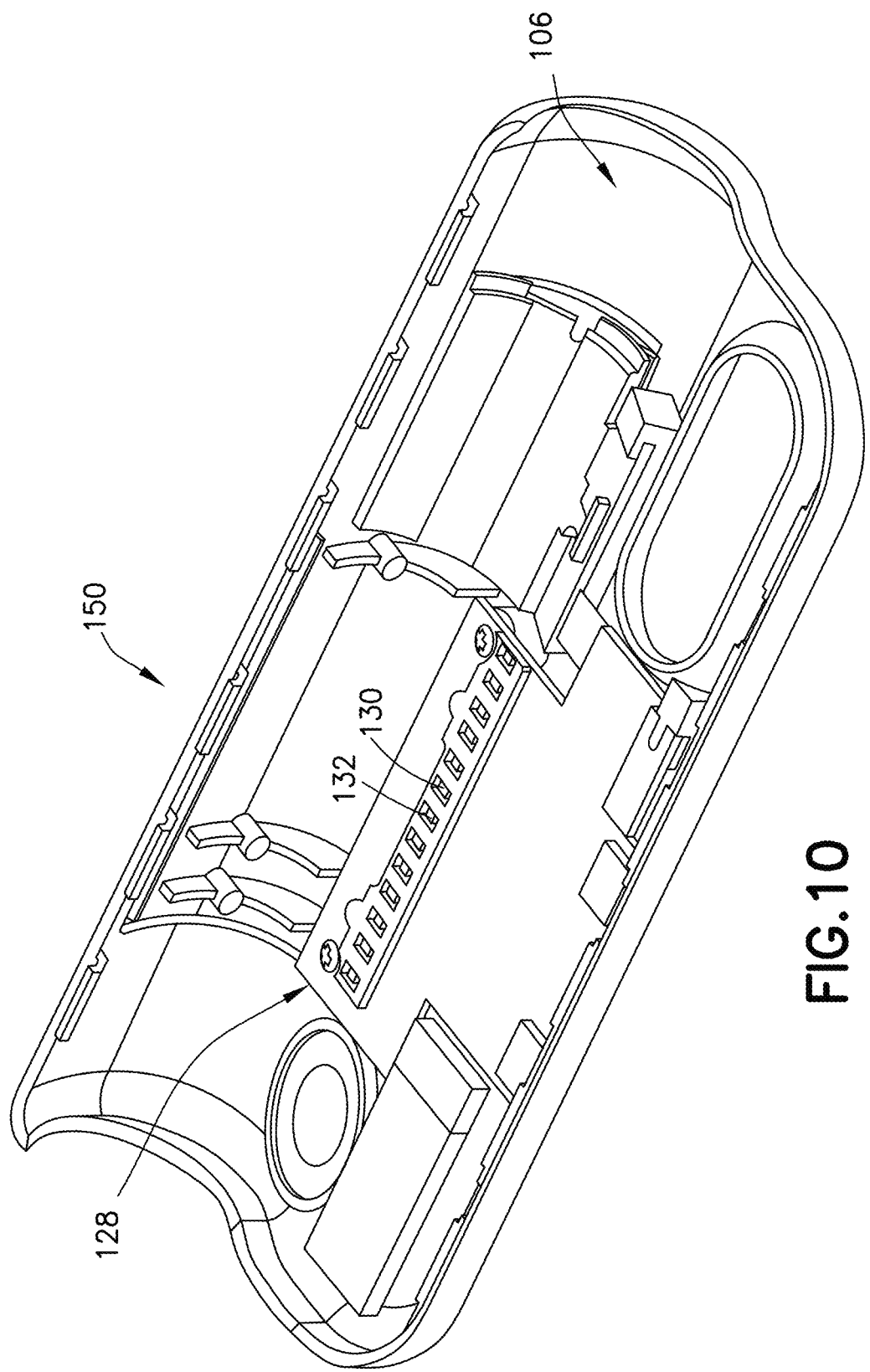
FIG. 10 is a perspective view of an inside surface of a cover of the smart wearable injection and/or infusion device shown in FIG. 6.
Figure 11:
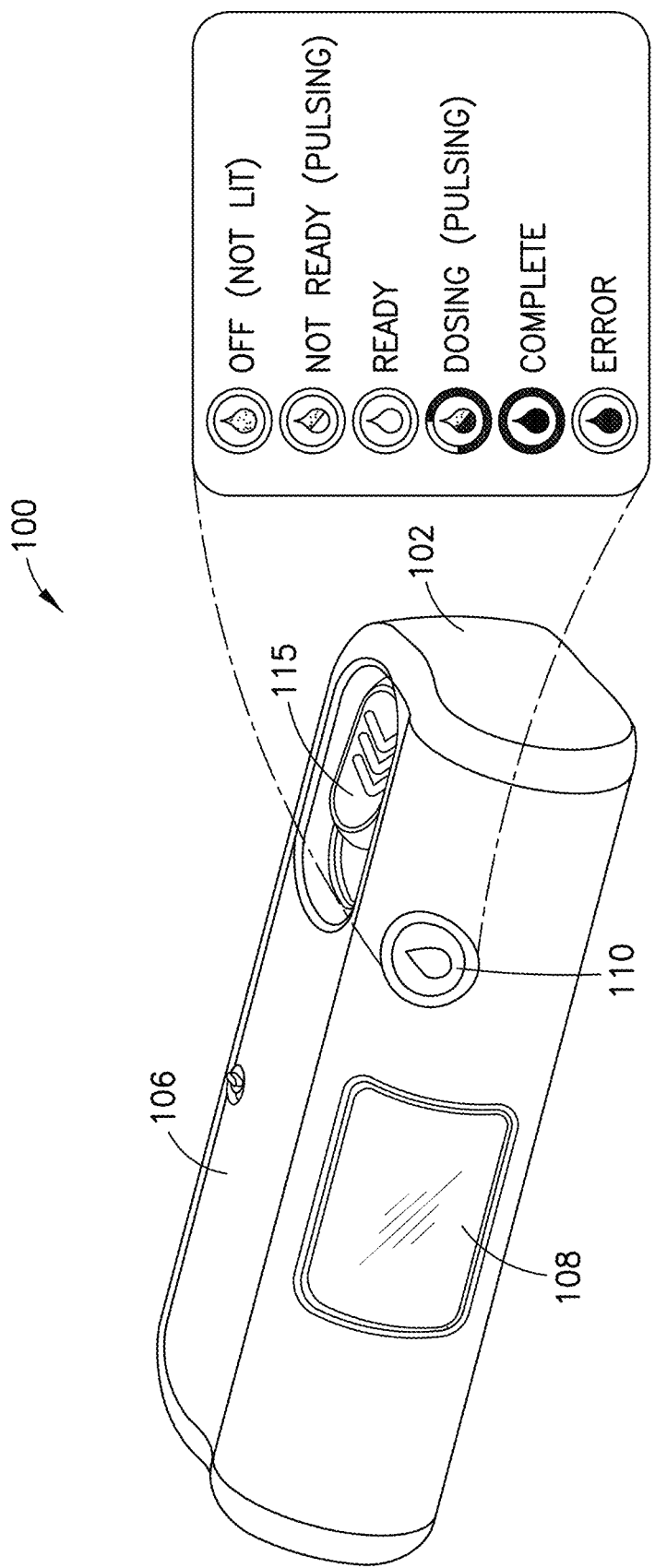
FIG. 11 is a front perspective view of a smart wearable injection and/or infusion device showing various states of an indicator.
Figure 12:
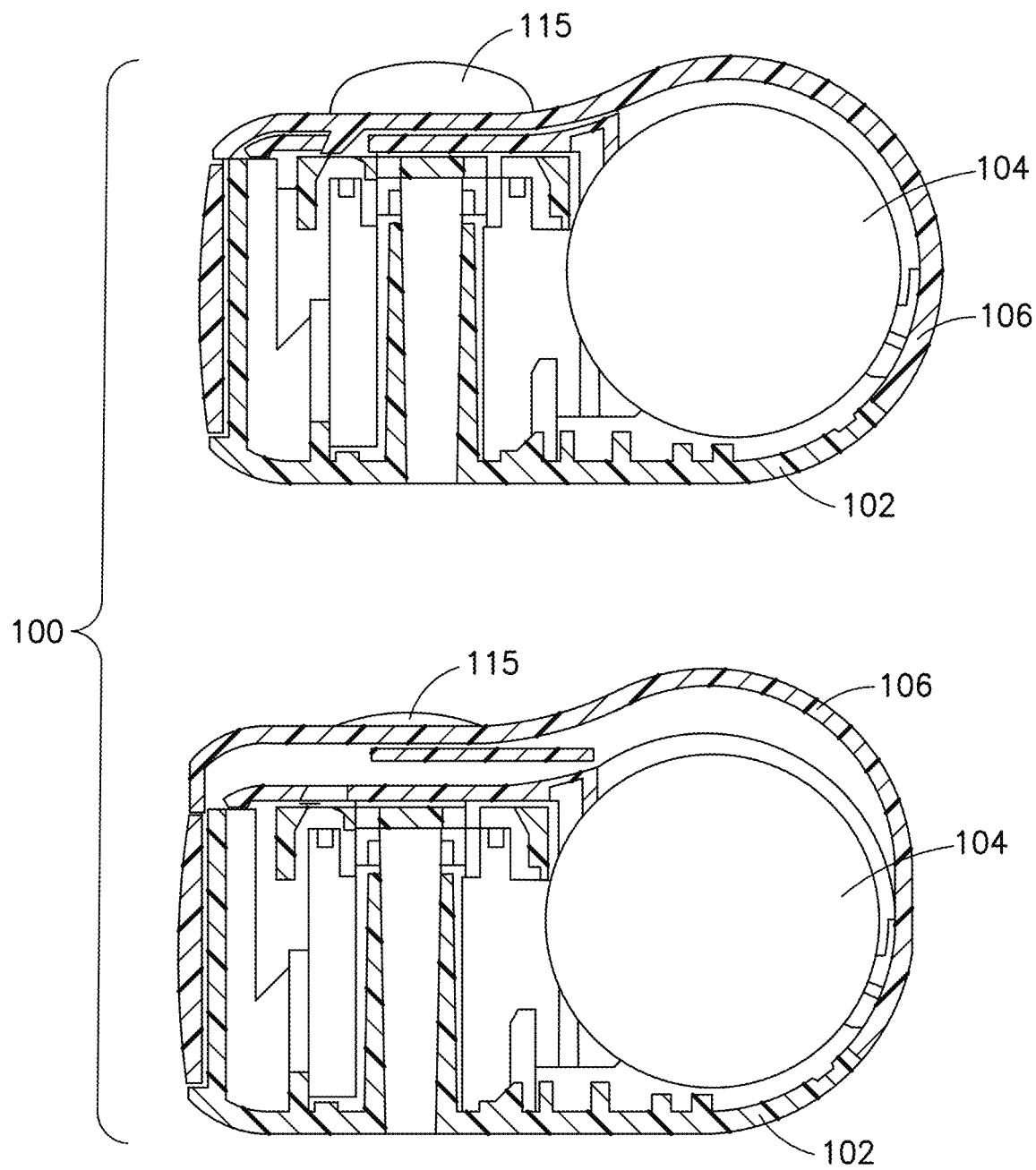
FIG. 12 shows cross-sectional views of various designs of a cover for use with a smart wearable injection and/or infusion device.

In some examples, such as shown in FIG. 10, the dose detection array 128 may be an infrared-based optical sensor array comprising one or more infrared emitters 130 (e.g. IR LEDs, and phototransistors or photodiodes) configured to emit electromagnetic energy in an infrared spectrum and one or more infrared detectors 132 configured to detect electromagnetic energy in the infrared spectrum. The dose detection array 128 may be integrated with the cover 106 such that removal of the cover 106 from the housing 102 also removes the dose detection array 128 from the housing 102.

With continued reference to FIG. 10, emitters 130 and detectors 132 may be interleaved on a common circuit board. The number of emitters 130 may be the same or different from the number of detectors 132. In some examples, emitters 130 and detectors 132 may be arranged in an alternating pattern, where each emitter/detector is positioned between a pair of detectors/emitters. The dose detection array 128 may be in electronic communication with a controller for controlling the optical components and processing the detector output to establish a location of the stopper. The wearable injection and/or infusion device 100 may further have other electronic devices to connect the controller to the dose detection array 128 (e.g. multiplexers, amplifiers, A/D, etc). The infrared spectrum offers improved immunity to external noise sources, such as visible light sources. Infrared light emitted from the emitters is also not visible to the user.

In use, a single emitter 130 may be activated to emit infrared light, while one or more detectors 132 detect the infrared light reflected from the container 104. This sequence can be repeated iteratively between different emitter/detector combinations. The sampling of all detectors 132 may be done simultaneously, or in a sequential manner. In some examples, emitters 130 may be active for less than 200 μs per measurement (0.02% duty cycle). The detector measurements are compared against a pre-existing set of reference measurements, and matched to the most likely reference point, which correlates to a stopper/plunger position. The number of reference measurement points may be higher than the number of detectors 132, in order to improve position resolution (e.g. 200 reference points using 6 detectors). In this manner, the dose detection array 128 functions similar to a multi-step encoder, such as a 200-step absolute position encoder. The method to match the acquired values to the reference minimizes the error between the collected data and the reference. Weighting methods may be used to selectively favor certain emitter/detector combinations at different times or positions during injection. Additional filtering may be employed to preprocess the data, such as to minimize ambient light effects. In some examples, the dose detection array 128 may have ~160 µm step resolution. To minimize effects of ambient infrared energy, a number of background measurements may be taken when no emitters are energized, so as to establish a detector baseline. This baseline value may then be subtracted from the detector measurements when an emitter is energized. Synchronous modulation techniques may also be utilized to isolate the target measurement from background energy levels.

In some examples, signal measurements may be processed using feature recognition methods to identify known signal features (e.g. local maxima or minima) which correspond to specific stopper/plunger positions, thus alleviating or minimizing the reliance on a pre-existing set of reference measurements. Feature recognition methods can include fuzzy logic and machine learning based techniques.

Figure 24:
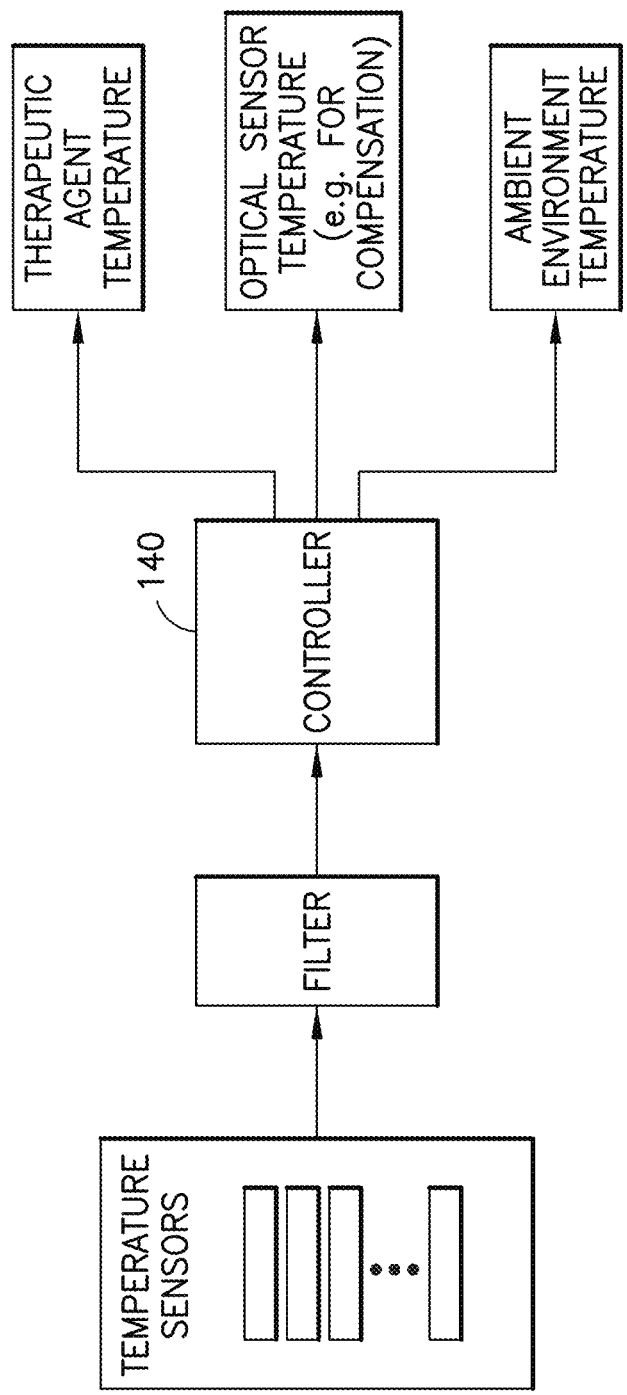
FIG. 24 is a schematic representation of a temperature detection and estimation of a smart wearable injection and/or infusion device.

The determination of dose progression may be founded on a position-based algorithm, from which a volume of the delivered dose can be calculated. The change in position of the stopper as a function of time can be used to calculate the velocity of the stopper, and therefore a rate of delivery of the therapeutic agent. The algorithm can compensate for known variations in the fluid delivery components, such as variability in the diameter and length of the container 104. Velocity data of the stopper/plunger can be used to determine whether the dosing procedure is stalled. For example, a minimum threshold (stall condition) may correspond with a minimum stopper/plunger velocity combined with any error sources (noise, ambient IR, etc.). For example, stall detection time may be dictated by a slowest acceptable delivery rate, such as 4 µl/s. FIGS. 17-20 show various performance parameters as a function of time As optical components are known to be temperature sensitive, temperature compensation may be applied using measurements from temperature sensors, to continuously correct for temperature-related measurement errors. With reference to FIG. 24, input from one or more temperature sensors may be passed through one or more filters to compensate for any temperature-related measurement errors.

In injection systems where the container 104 must first translate a fixed distance to pierce the septum, the dose detection array can also be used to detect the position of the entire container 104 (including plunger). A separate reference measurement set can be utilized to determine the position of the entire container 104. Once the container is detected to be in the pierced state, the algorithm can switch to the reference set used to detect plunger position.

Premature Removal Detection

In some examples, computed position and velocity data can be used to determine whether the device was prematurely removed from the injection site. For example, a maximum velocity threshold may correspond to the maximum expected stopper/plunger velocity when injected into a body (i.e. a high pressure site). Velocities higher than this threshold may correspond to injection in air (i.e. a low pressure site). A large, sudden unexpected change in position or velocity, can thus be used to indicate an undesirable change at the injection site (e.g. from premature removal or needle withdrawal).

Temperature Measurement

In some examples, the wearable injection and/or infusion device 100 may be configured to measure temperature, such as the temperature of the therapeutic agent inside the container 104. For example, one or more temperature sensors 126 may be used to detect a temperature of the container 104. Using this temperature data, a temperature of the therapeutic agent inside the container 104 may be predicted based on at least one of a plurality of factors, such as temperature at one or more locations within the injector relative to the temperature of the container, spatial temperature gradient within the injector, rate of change of temperature at the measurement locations of the container (i.e. temporal gradient). Temperature sensor data may be used to predict or estimate ambient environment temperature during transient temperature conditions. By estimating the ambient environment temperature, versus a local temperature within the device, the temperature of the therapeutic agent inside the container can be better predicted over time. Temperature data may be used to indicate whether the wearable injection and/or infusion device 100 is ready to perform a dosing procedure. For example, certain therapeutic agents can only be delivered if they are at a predetermined temperature (or temperature range). The wearable injection and/or infusion device 100 may prevent delivery of the therapeutic agent if the therapeutic agent is above/below such predetermined temperature (or temperature range). In some examples, the wearable injection and/or infusion device 100 may permit delivery of the therapeutic agent that is outside of a predetermined temperature (or temperature range) using an augmented dosing procedure, such as an increased or decreased delivery rate.

Temperature data can also be combined with dose progression data to detect or estimate whether an abnormal delivery rate (or stall in dose progression) is likely caused by a temperature-related change in therapeutic agent viscosity (e.g. stall due to increase in viscosity at cold temperatures). In these scenarios, changes in a temperature data can be used to indicate whether the abnormal delivery condition is expected to resolve (e.g. injection is currently stalled but likely to resume since temperatures are increasing), such as to prevent premature removal for temporary delivery disruptions.

External Communication

Figure 13:
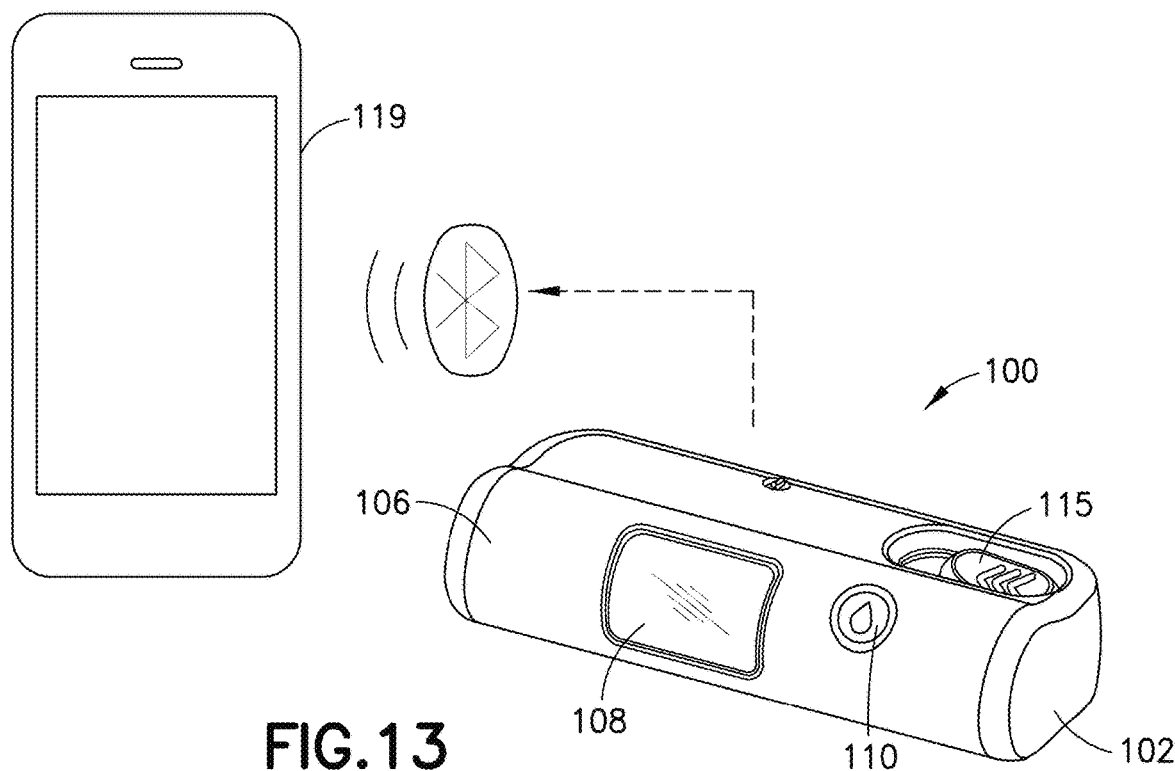
FIGS. 13-14 show smart wearable injection and/or infusion devices configured for wireless communication with a remote device.
Figure 14:
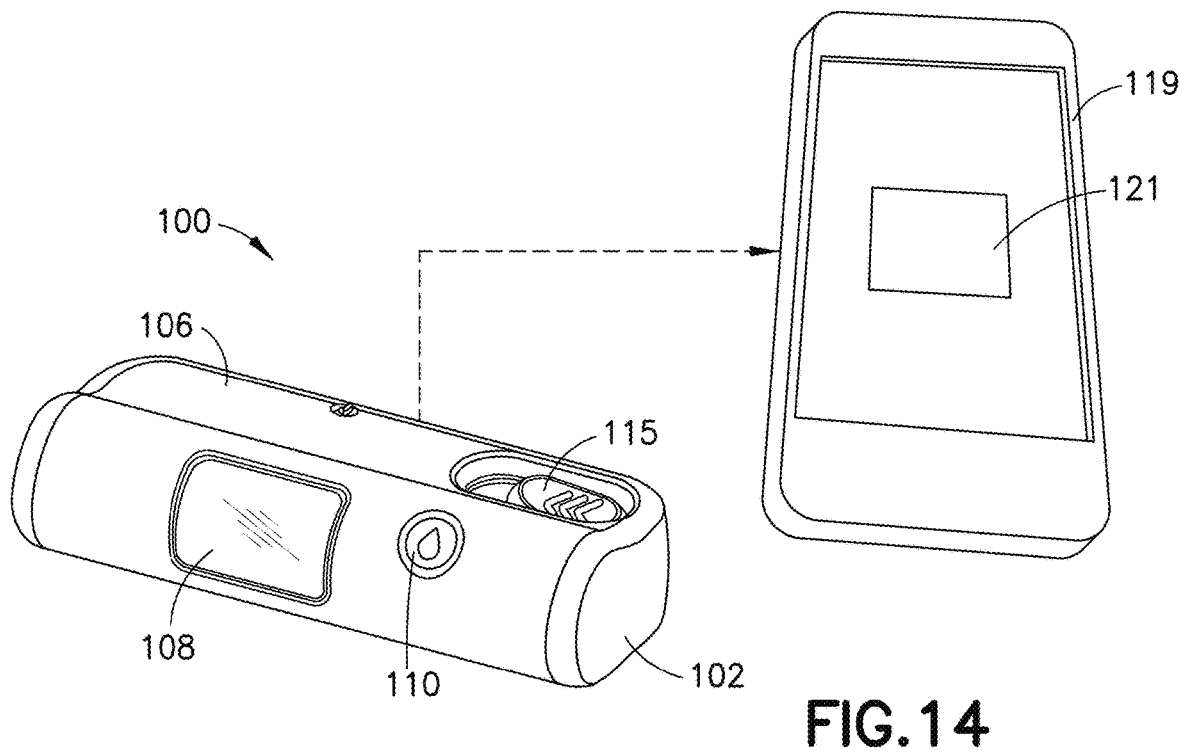

In some examples, the wearable injection and/or infusion device 100 may be configured for external communication with a remote device 119 via a network, such as shown in FIGS. 13-14. The communication may be a one-way communication, wherein the wearable injection and/or infusion device 100 is configured to only send information to the remote device 119 or receive information from the remote device 119. In other examples, the wearable injection and/or infusion device 100 may be configured for two-way communication with the remote device 119, wherein the wearable injection and/or infusion device 100 is configured to both send information to the remote device 119 and receive information from the remote device 119. In some examples, the wearable injection and/or infusion device 100 may have a transceiver-like component (e.g., a transceiver, a separate receiver and transmitter, etc.) that enables the wearable injection and/or infusion device 100 to communicate with the remote device 119, such as via a wired connection, a wireless connection, or a combination of wired and wireless connections. The transceiver-like component can permit the wearable injection and/or infusion device 100 to receive information from the remote device 119 and/or provide information to the remote device 119.

In some examples, the network may include one or more wired and/or wireless networks. For example, network may include a cellular network (e.g., a long-term evolution (LTE) network, a third generation (3G) network, a fourth generation (4G) network, a code division multiple access (CDMA) network, etc.), a public land mobile network (PLMN), a local area network (LAN), a wide area network (WAN), a metropolitan area network (MAN), a telephone network (e.g., the public switched telephone network (PSTN)), a private network, an ad hoc network, an intranet, the Internet, a fiber optic-based network, a cloud computing network, and/or the like, and/or a combination of these or other types of networks.

Figure 15:
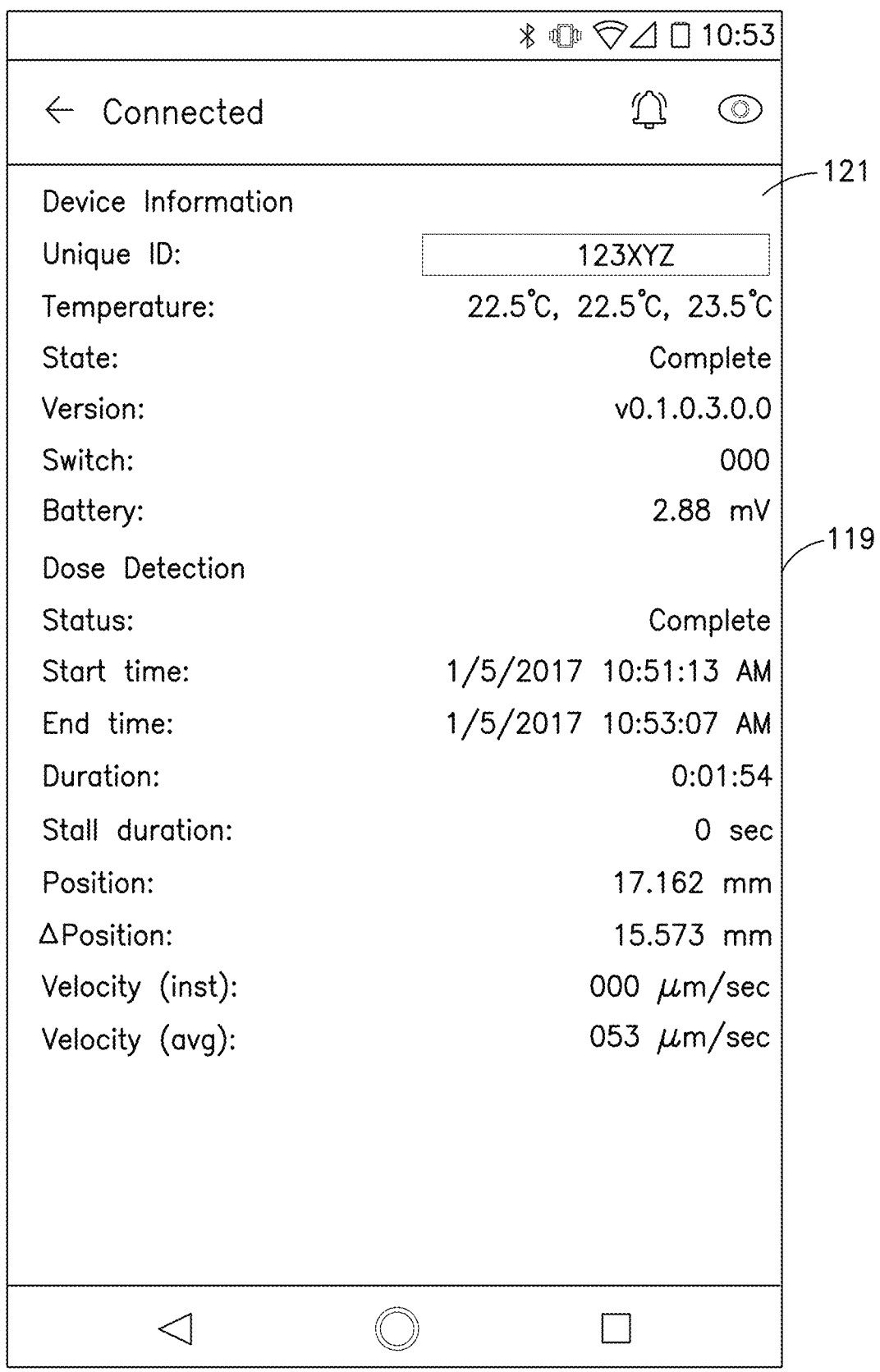
FIG. 15 is a screenshot of a graphical user interface of a mobile device application configured for use with a smart wearable injection and/or infusion device.
Figure 16:
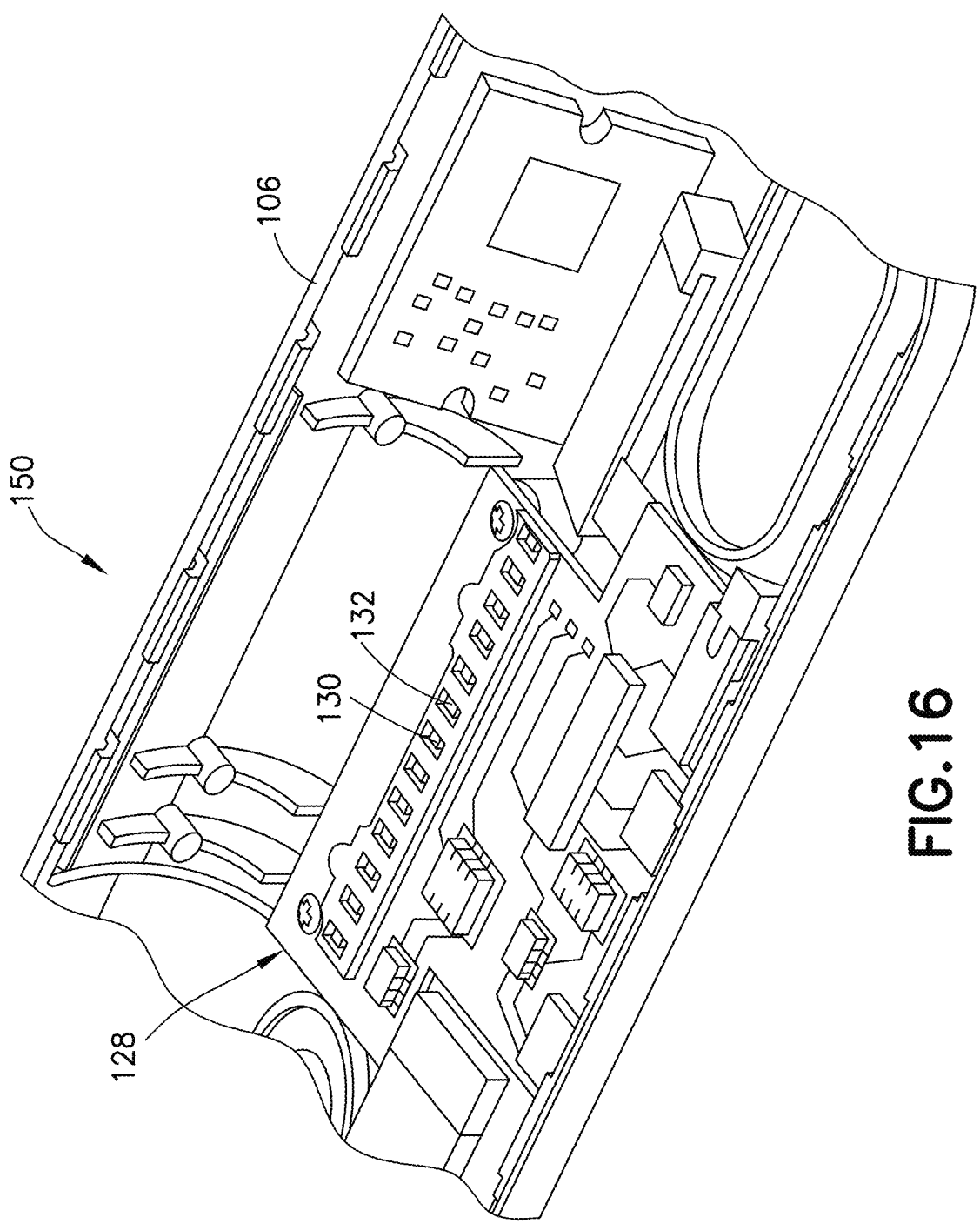
FIG. 16 is a detailed view of an optical sensing array for use with smart wearable injection and/or infusion device.
Figure 17:
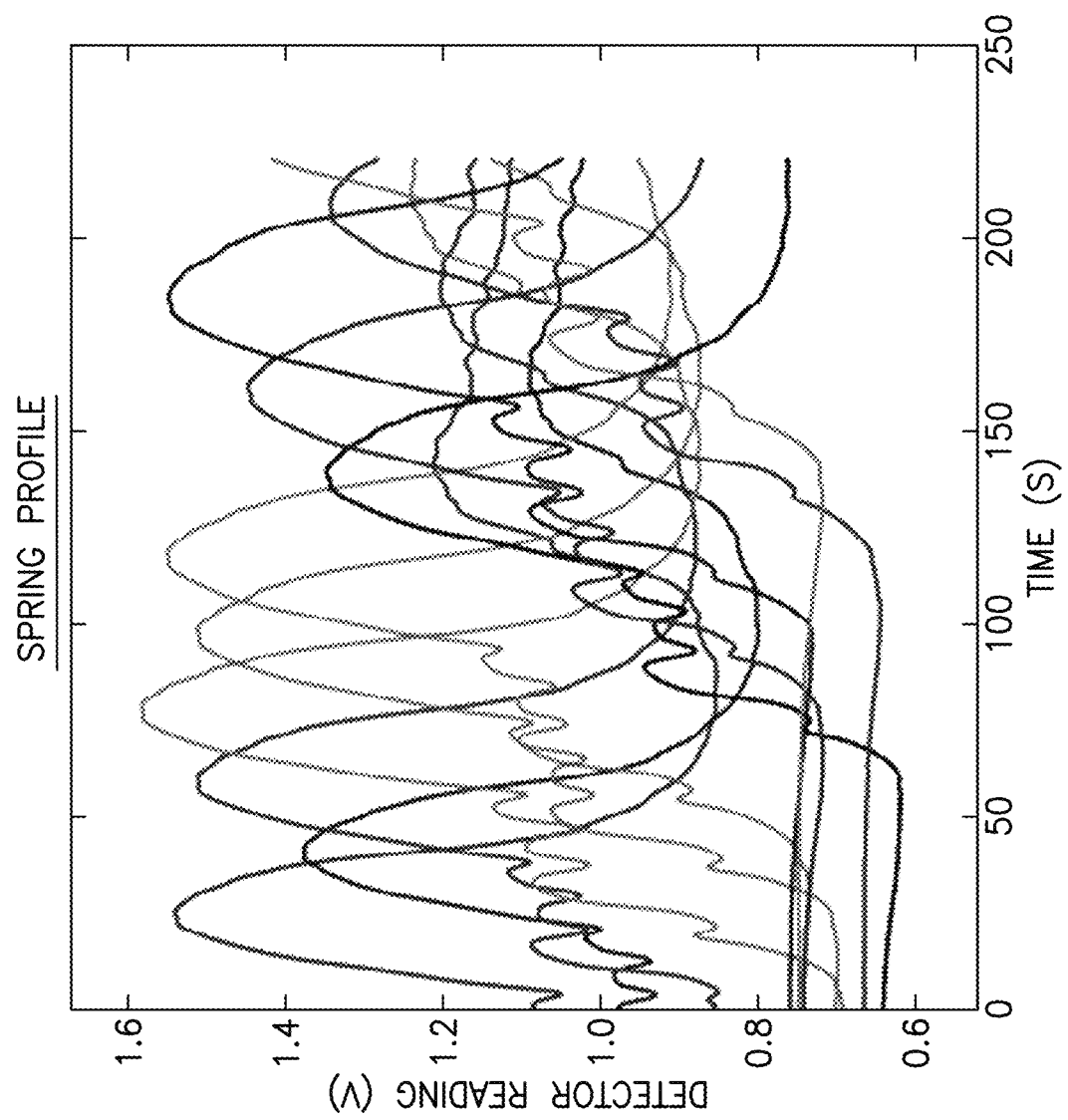
FIGS. 17-20 show various performance parameters of a smart wearable injection and/or infusion device as a function of time.
Figure 18:
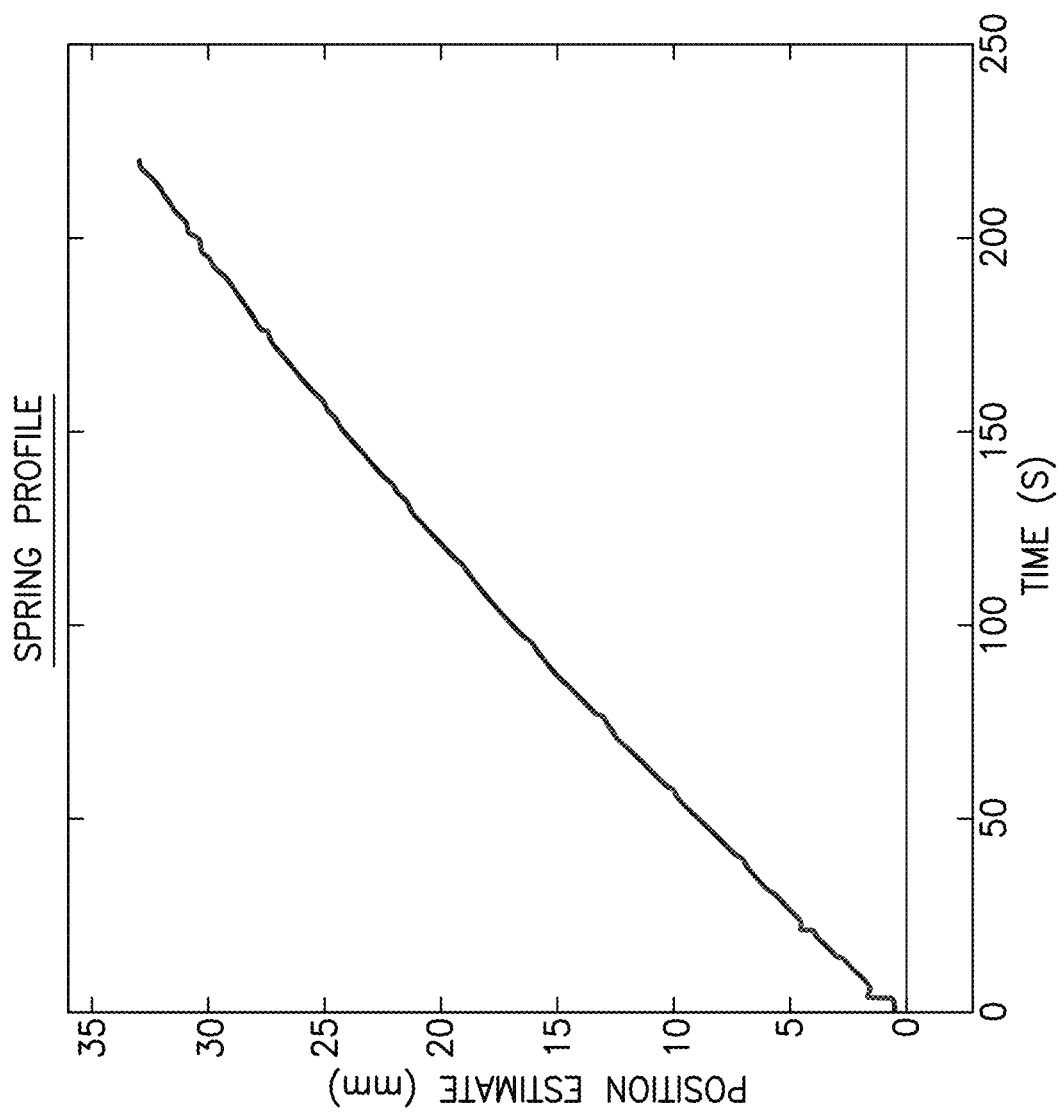
Figure 19:
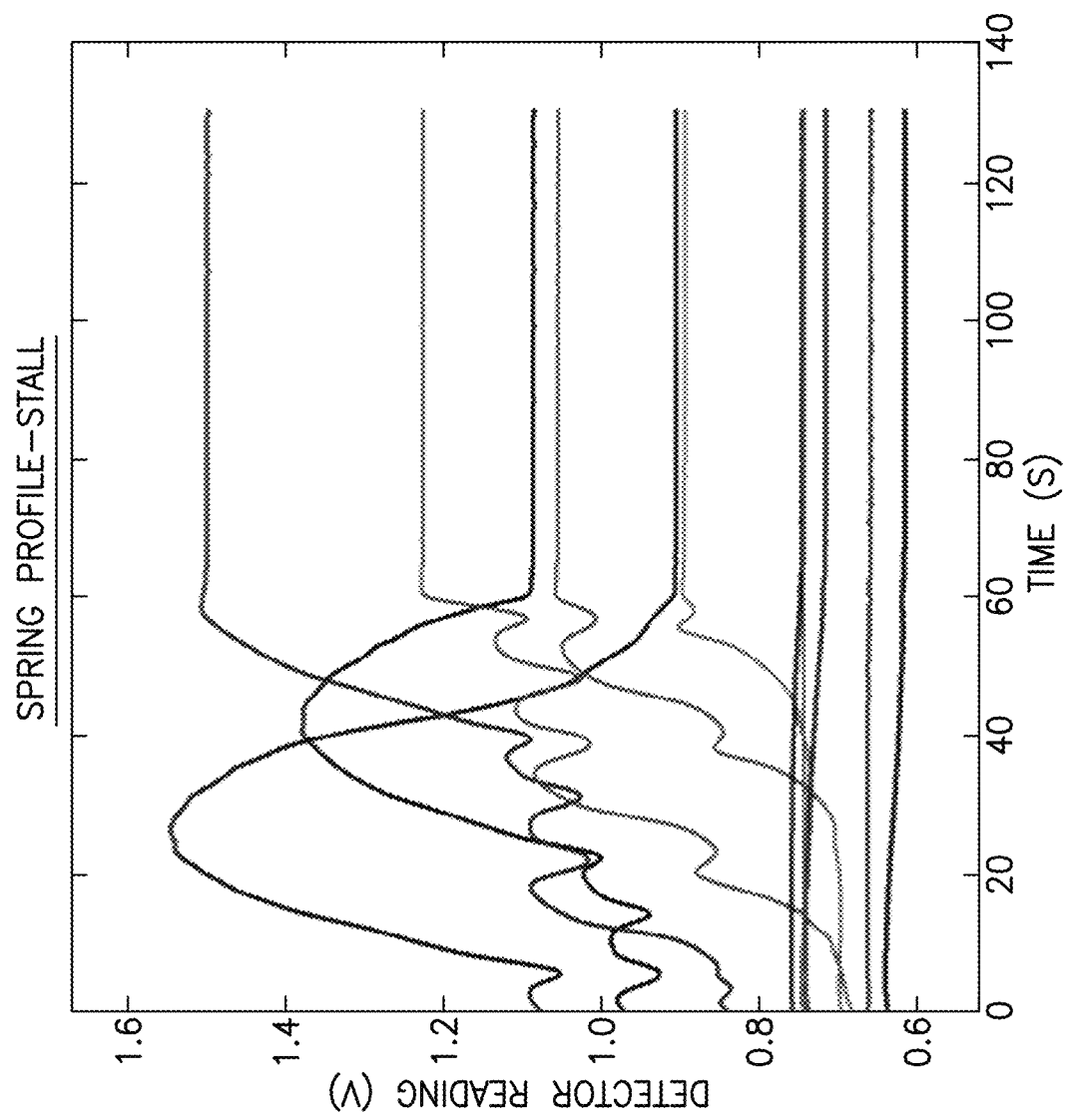
Figure 20:
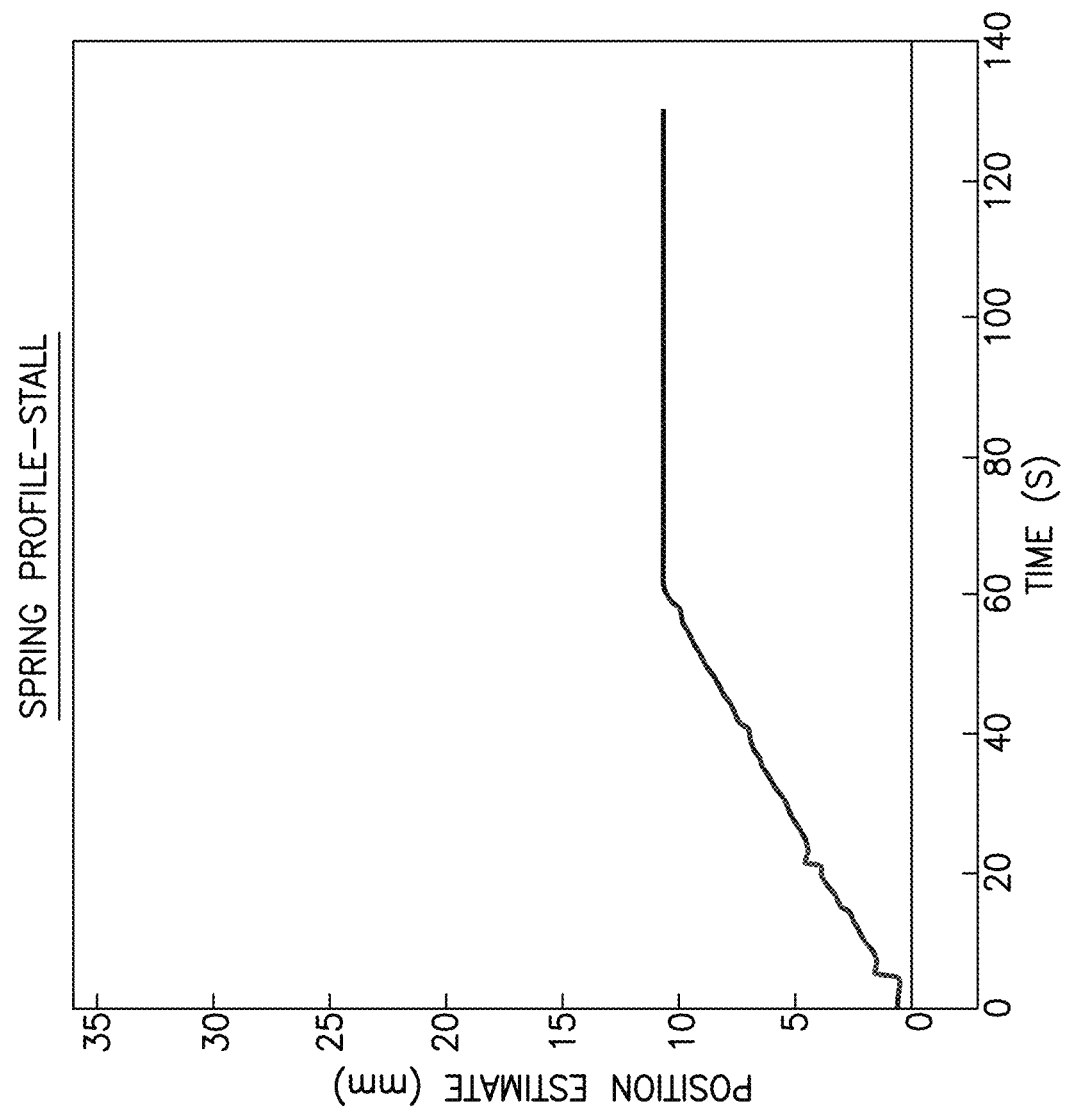
Figure 21:
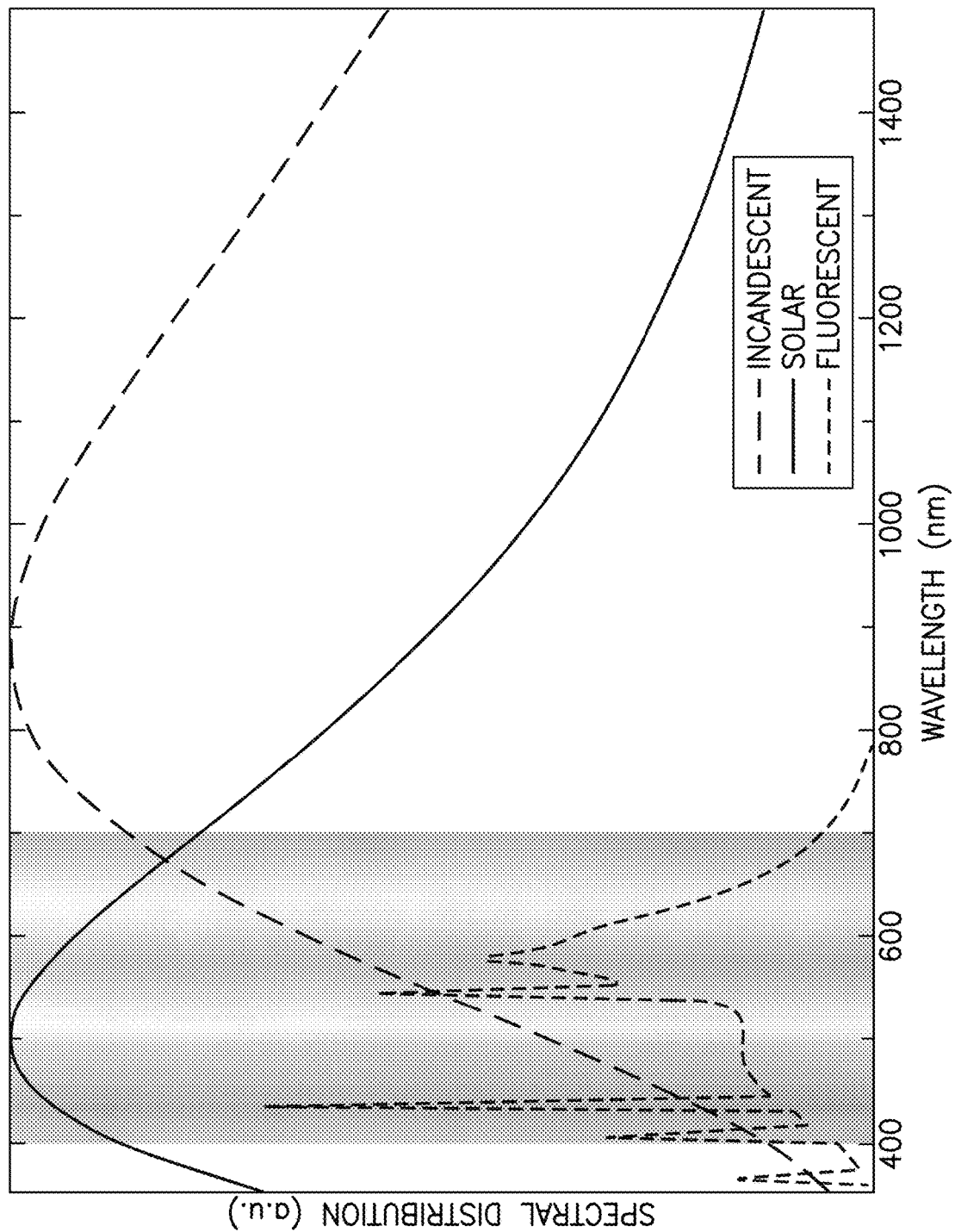
FIGS. 21-22 show a spectral distribution as a function of wavelength for various types of lighting.
Figure 22:
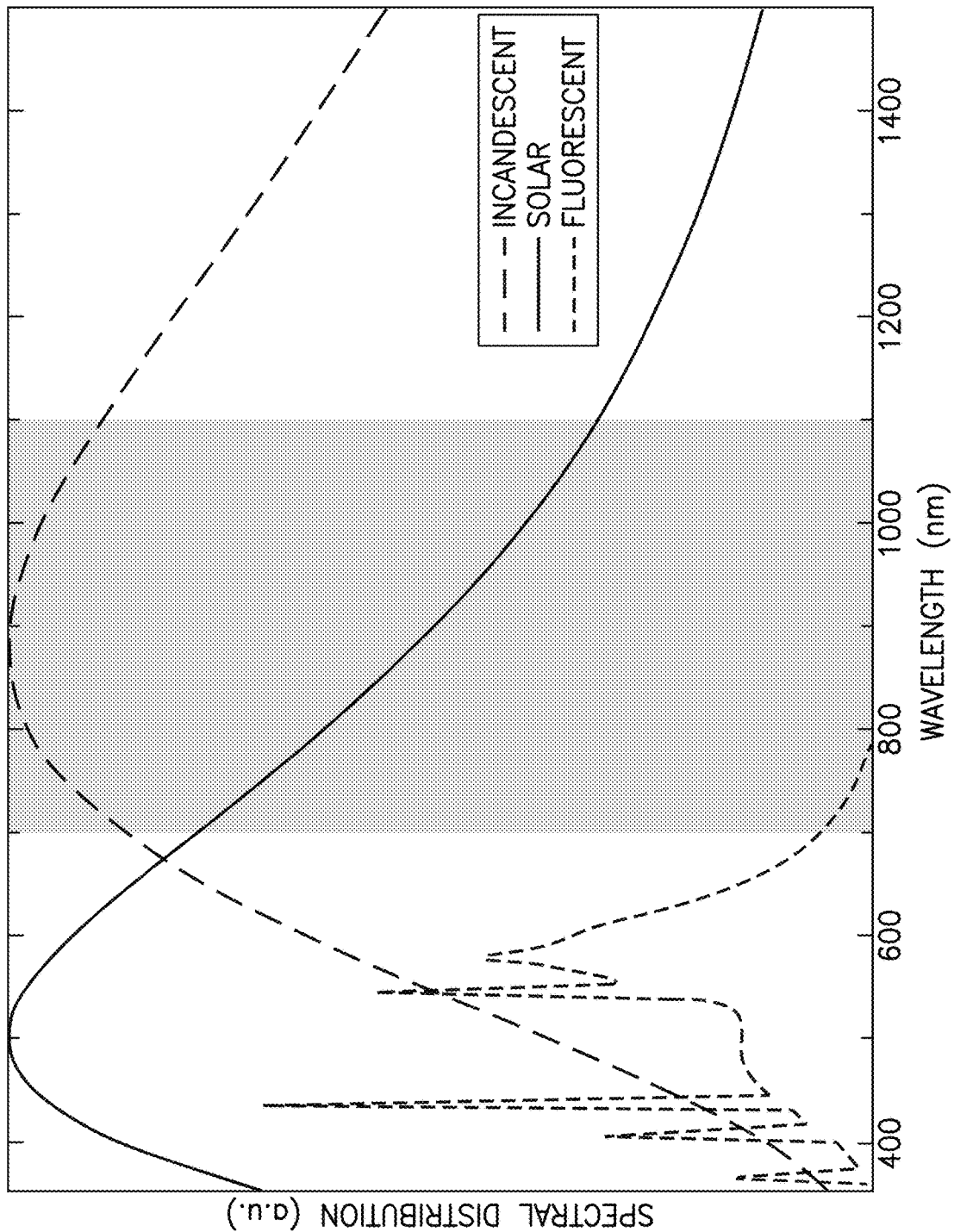

In some examples, the wearable injection and/or infusion device 100 may be configured for wireless external communication, such as using a Bluetooth or Wi-Fi or cellular communication protocol, with an application 121 on a remote device 119, such as a tablet or a mobile telephone or a server-based application. The application 121 on the remote device 119 may be configured to display real-time data regarding the performance of the wearable injection and/or infusion device 100. In some examples, the application 121 on the remote device 119 may be configured to display any data associated with the wearable injection and/or infusion device 100 (FIG. 15). In some examples, the wearable injection and/or infusion device 100 may have a BLE/MCU radio for wireless external communication with the remote device.

The remote device may be configured to provide contextual instructions to patient during use of the wearable injection and/or infusion device 100. For example, the remote device may provide instructions to patient on how to set up and initiate a dosing procedure using the wearable injection and/or infusion device 100. In some examples, the remote device may indicate to the patient that a dosing procedure is ongoing and provide status indication of various stages of the dosing procedure. In further examples, the remote device may provide instructions to the patient on a procedure to be followed in an extraordinary event, such as in an instance when the dosing procedure may stall. The wearable injection and/or infusion device 100 may be configured to send information, using the remote device, to a third party, such as the patient's medical provider or medical insurance company about time, date, and volume of the therapeutic agent delivered to the patient. The wearable injection and/or infusion device 100 may contact such third party in case of an extraordinary event, such as by sending a text alert or dialing a telephone number of the third party.

Data from the wearable injection and/or infusion device 100 may be transmitted to the remote device in real time and/or the data may be stored in a remote database for post-delivery use. In some examples, the remote device may be used to run a safety protocol prior to when the wearable injection and/or infusion device 100 initiates a dosing procedure. For example, the remote device can check for drug recalls, verify that the correct therapeutic agent is used, and/or verify the time and volume of the last dosing procedure. The wearable injection and/or infusion device 100 may be blocked from initiating a new dosing procedure depending on whether the safety protocol run on the remote device detects any abnormalities.

Enhanced Visual Indicators

In some examples, the wearable injection and/or infusion device 100 may have one or more enhanced electronic indicators. For example, the wearable injection and/or infusion device 100 may have one or more visual indicators, such as an LED-based indicator with 3-colors (blue, red, white). Alternatively, or in addition, the wearable injection and/or infusion device 100 may have one or more audible indicators, such as a piezo-based buzzer with chimes/beeps.

With a visual indicator, a range of visual messages may be delivered to the user regarding the status of the wearable injection and/or infusion device and its performance. For example, a color of the visual indicator can be used to indicate a state of the wearable injection and/or infusion device 100, such as whether the device is powered on, whether a dosing procedure is ongoing, etc. Alternatively, or in addition, the visual indicator may be operated between a steady-state and flashing operation to indicate a state of the wearable injection and/or infusion device 100. A speaker port may be provided in a housing of the wearable injection and/or infusion device 100 to deliver audible messages to the user.

Although the invention has been described in detail for the purpose of illustration based on what are currently considered to be the most practical and preferred examples, it is to be understood that such detail is solely for that purpose and that the invention is not limited to the disclosed examples, but, on the contrary, is intended to cover modifications and equivalent arrangements that are within the spirit and scope of the present disclosure. For example, it is to be understood that the present invention contemplates that, to the extent possible, one or more features of any example can be combined with one or more features of any other example.

What is claimed is:

1. A delivery device for delivering a medical fluid to a patient, the delivery device comprising:
   a housing configured for receiving a container at least partially filled with the medical fluid;
   a cover removably connectable to the housing;
   a drive mechanism associated with the housing configured for delivering the medical fluid from the container to the patient in a dosing procedure; and
   a module configured for detecting at least one of a property of the dosing procedure or a property of the medical fluid, the module comprising a dose detection array configured for detecting an initiation, progression, and completion of the dosing procedure based on a position of a stopper within the container;
   wherein the dose detection array comprises an optical sensor array integrated with the cover, such that removal of the cover from the housing results in removal of the optical sensor array from the housing.

2. The delivery device of claim 1, wherein, based on detecting a change in the position of the stopper as a function of time, the dose detection array is configured for measuring a rate of delivery of the medical fluid to the patient.

3. The delivery device of claim 2, wherein the module is configured to stop the drive mechanism if the rate of delivery of the medical fluid measured by the dose detection array is below a minimum threshold or above a maximum threshold.

4. The delivery device of claim 1, wherein the optical sensor array is configured to detect an actual volume of the medical fluid in the container or estimate a volume of the medical fluid in the container based on the position of the stopper within the container.

5. The delivery device of claim 4, wherein the optical sensor array comprises one or more infrared emitters configured to emit electromagnetic energy in an infrared spectrum and one or more infrared detectors configured to detect the electromagnetic energy in the infrared spectrum.

6. The delivery device of claim 1, wherein the module further comprises at least one temperature sensor configured for measuring a temperature of the medical fluid within the container based on a temperature of the container, and wherein an output of the dose detection array is a function of an output of the at least one temperature sensor.

7. The delivery device of claim 6, wherein the temperature of the medical fluid is a function of an ambient environment temperature outside the housing of the delivery device and a local temperature within the housing of the delivery device.

8. The delivery device of claim 6, wherein the module is configured to prevent actuation of the drive mechanism if the temperature of the medical fluid within the container is below a minimum threshold or above a maximum threshold.

9. The delivery device of claim 1, wherein the module further comprises at least one activation detection switch configured for detecting the initiation of the dosing procedure and at least one completion detection switch configured for detecting the completion of the dosing procedure.

10. The delivery device of claim 9, wherein the at least one activation detection switch is configured to detect at least one of a position or a velocity of at least one component of the drive mechanism and wherein the at least one completion detection switch is configured to detect at least one of a position or a velocity of at least one component of the drive mechanism.

11. The delivery device of claim 10, wherein the at least one activation detection switch is a mechanical sensor in direct physical contact with the at least one component of the drive mechanism or an optical sensor without direct physical contact with the at least one component of the drive mechanism.

12. The delivery device of claim 10, wherein the at least one completion detection switch is a mechanical sensor in direct physical contact with the at least one component of the drive mechanism or an optical sensor without direct physical contact with the at least one component of the drive mechanism.

13. The delivery device of claim 1, wherein the module further comprises a communication element configured for external communication with a remote device via a wired connection, a wireless connection, or a combination of the wired connection and the wireless connection.

14. The delivery device of claim 13, wherein the communication element is a one-way communication element configured to send information to the remote device or receive information from the remote device, or a two-way communication element configured to send information to the remote device and receive information from the remote device.

15. The delivery device of claim 13, wherein the remote device is configured to provide at least one of contextual instructions for using the delivery device, safety protocol information about the dosing procedure, or a status indication of at least one stage of the dosing procedure.

16. The delivery device of claim 1, wherein the module further comprises one or more indicators configured for providing at least one of information about a state of the dosing procedure or operation instructions to a user.

17. The delivery device of claim 16, wherein the one or more indicators comprises at least one visual indicator having at least one light.

18. The delivery device of claim 17, wherein the at least one light is a single or multi-color light-emitting diode configured for at least one of steady state or flashing operation.

19. The delivery device of claim 16, wherein the one or more indicators comprises at least one audible indicator configured for delivering an audible message to the user.

* * * * *